US012782369B2

(12) United States Patent
Webster

(10) Patent No.: US 12,782,369 B2
(45) Date of Patent: *Nov. 3, 2026

(54) TWO PART ASSEMBLY

(71) Applicant: Zomedica Biotechnologies LLC, Ann Arbor, MI (US)

(72) Inventor: James Russell Webster, Minnetonka, MN (US)

(73) Assignee: Zomedica Biotechnologies LLC, Ann Arbor, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/608,269

(22) Filed: Mar. 18, 2024

(65) Prior Publication Data

US 2024/0219409 A1 Jul. 4, 2024

Related U.S. Application Data

(63) Continuation of application No. 17/014,694, filed on Sep. 8, 2020, now Pat. No. 11,933,793, which is a (Continued)

(51) Int. Cl.

*G01N 33/78* (2006.01)
*B01L 3/00* (2006.01)

(Continued)

(52) U.S. Cl.

CPC ........ *G01N 33/78* (2013.01); *B01L 3/502738* (2013.01); *G01N 29/022* (2013.01);

(Continued)

(58) Field of Classification Search

None

See application file for complete search history.

(56) References Cited

U.S. PATENT DOCUMENTS 4,361,026 A 11/1982 Muller et al.
4,654,127 A 3/1987 Baker et al.

(Continued)

FOREIGN PATENT DOCUMENTS

CA 2344755 11/2001
CN 1566933 A 1/2005

(Continued)

OTHER PUBLICATIONS

Yafei, "Principles, Design and Application of Film Bulk Acoustic Resonator Film Bulk Acoustic Resonator," Shanghai Jiao Tong University Press, Jan. 2011, original and English translation, 12 pages.

(Continued)

*Primary Examiner* — Brian R Gordon

(74) *Attorney, Agent, or Firm* — Standley Law Group LLP; Jeffrey S. Standley; Bryan P. Finneran

(57) ABSTRACT

A device that includes a first portion, the first portion including at least one fluid channel; a fluid actuator; and an introducer, a second portion, the second portion including at least one well, the well containing at least one material, wherein one of the first or second portion is moveable with respect to the other, wherein the introducer is configured to obtain at least a portion of the material from the at least one well and deliver it to the fluid channel, and wherein the fluid actuator is configured to move at least a portion of the material in the fluid channel.

18 Claims, 19 Drawing Sheets

Related U.S. Application Data continuation of application No. 14/893,388, filed as application No. PCT/US2014/039400 on May 23, 2014, now abandoned.

(60) Provisional application No. 61/826,845, filed on May 23, 2013.

(51) Int. Cl.

*G01N 29/02* (2006.01)
*G01N 29/036* (2006.01)
*G01N 29/22* (2006.01)
*G01N 33/543* (2006.01)

(52) U.S. Cl.

CPC ......... *G01N 29/036* (2013.01); *G01N 29/222* (2013.01); *G01N 33/54386* (2013.01); *B01L 2200/027* (2013.01); *B01L 2300/0816* (2013.01); *B01L 2300/0867* (2013.01); *B01L 2400/0487* (2013.01); *B01L 2400/0644* (2013.01); *B01L 2400/065* (2013.01); *G01N 2291/012* (2013.01); *G01N 2291/0255* (2013.01); *G01N 2291/0256* (2013.01); *G01N 2291/0426* (2013.01); *G01N 2333/59* (2013.01)

(56) References Cited

U.S. PATENT DOCUMENTS 4,999,284 A 3/1991 Ward et al.
5,404,628 A 4/1995 Ketcham
5,405,510 A 4/1995 Betts et al.
5,693,233 A 12/1997 Schembri
5,821,833 A 10/1998 Lakin
5,894,647 A 4/1999 Lakin
5,922,591 A 7/1999 Anderson et al.
5,932,953 A 8/1999 Drees et al.
5,936,150 A 8/1999 Kobrin et al.
5,942,958 A 8/1999 Lakin
6,086,740 A * 7/2000 Kennedy ........... B01L 3/502715 204/601
6,107,721 A 8/2000 Lakin
6,114,635 A 9/2000 Lakin et al.
6,132,685 A * 10/2000 Kercso ................. G01N 35/028 422/65
6,207,031 B1 * 3/2001 Adourian .......... B01L 3/502753 204/603
6,235,488 B1 5/2001 Tom-May et al.
6,291,931 B1 9/2001 Lakin
6,296,020 B1 10/2001 McNeely
6,322,683 B1 11/2001 Wolk
6,441,703 B1 8/2002 Panaski
6,495,369 B1 * 12/2002 Kercso ................. G01N 35/028 422/65
6,537,501 B1 3/2003 Holl
6,686,128 B1 2/2004 Lakin et al.
6,720,844 B1 4/2004 Lakin
7,241,421 B2 7/2007 Webster et al.
7,247,274 B1 * 7/2007 Chow .................. B01J 19/0093 422/50
7,288,229 B2 10/2007 Turner et al.
7,353,695 B2 4/2008 Fitch et al.
7,405,054 B1 7/2008 Hasenbank et al.
7,419,821 B2 9/2008 Davis et al.
7,454,958 B2 11/2008 Ellson
7,468,138 B2 12/2008 Weinberg et al.
7,666,687 B2 2/2010 Webster et al.
7,695,681 B2 4/2010 Wang et al.
7,963,151 B2 6/2011 Godfrey et al.
8,040,494 B2 10/2011 Ermantraut et al.
8,066,944 B2 11/2011 Carter et al.
8,084,002 B2 12/2011 Carter et al.
8,154,093 B2 4/2012 Bradley et al.
8,309,039 B2 11/2012 Webster et al.
8,309,364 B2 11/2012 Miller et al.
8,408,875 B2 4/2013 Johal et al.
8,467,039 B2 6/2013 Ermantraut et al.
9,032,782 B1 5/2015 Van Deusen et al.
9,895,692 B2 2/2018 Battrell
10,234,425 B2 3/2019 Salvati et al.
2001/0027745 A1 10/2001 Weigl
2001/0049148 A1 12/2001 Wolk
2002/0009392 A1 * 1/2002 Wolk ................. G01N 35/1004 204/453
2002/0121529 A1 * 9/2002 Hoummady .......... B01L 3/0268 222/113
2003/0027225 A1 * 2/2003 Wada ............... G01N 27/44717 435/287.2
2003/0091477 A1 5/2003 Paul
2003/0162304 A1 8/2003 Dority
2004/0262162 A1 12/2004 Roach
2005/0232820 A1 * 10/2005 Reed ....................... B01L 3/563 422/552
2006/0054941 A1 3/2006 Lu et al.
2006/0062696 A1 * 3/2006 Chow ............... B01L 3/502746 422/400
2006/0125489 A1 6/2006 Feucht et al.
2006/0133953 A1 6/2006 Zhang et al.
2006/0222568 A1 10/2006 Wang et al.
2007/0086922 A1 * 4/2007 Andersson ............ B01L 3/0268 422/400
2007/0120625 A1 5/2007 Larson et al.
2007/0210349 A1 9/2007 Lu et al.
2008/0182301 A1 7/2008 Handique
2009/0017491 A1 1/2009 Lemme et al.
2009/0059230 A1 3/2009 Takada et al.
2009/0074951 A1 3/2009 Bellew et al.
2009/0170119 A1 7/2009 Lee et al.
2009/0282092 A1 11/2009 Warthoe
2010/0105079 A1 4/2010 Warthoe
2010/0127600 A1 5/2010 Loschonsky et al.
2010/0189601 A1 7/2010 Crawford
2010/0218353 A1 9/2010 Kolosov et al.
2010/0291668 A1 11/2010 Bertrand et al.
2011/0008776 A1 1/2011 Warthoe et al.
2011/0092373 A1 * 4/2011 Colston, Jr. ....... B01L 3/502715 506/38
2011/0269249 A1 11/2011 Warthoe et al.
2011/0316522 A1 12/2011 Shinobu et al.
2012/0149603 A1 6/2012 Cooney
2012/0164753 A1 6/2012 Johnston et al.
2012/0190128 A1 7/2012 Nikbakht et al.
2012/0196384 A1 8/2012 Zhang et al.
2012/0304776 A1 12/2012 Novotny
2013/0224732 A1 8/2013 Lee et al.
2014/0127826 A1 5/2014 Johal et al.
2014/0154697 A1 6/2014 Johal et al.
2015/0045234 A1 * 2/2015 Stone ................. G01N 35/1095 435/6.1
2015/0141291 A1 * 5/2015 Zhou ...................... G01N 35/10 435/6.12
2015/0377834 A1 12/2015 Salvati et al.
2016/0091506 A1 3/2016 Webster
2018/0015467 A1 1/2018 Liang
2019/0187098 A1 6/2019 Salvati et al.
2021/0378643 A1 12/2021 Roswech
2022/0008924 A1 1/2022 Clime
2022/0008928 A1 1/2022 Colston
2022/0065890 A1 3/2022 Carrillo
2022/0203371 A1 6/2022 Handique
2022/0347680 A1 11/2022 Wernerehl

FOREIGN PATENT DOCUMENTS

CN 101305279 A 11/2008
CN 202159037 U 3/2012
CN 103403583 A 11/2013
CN 110694700 A 5/2014
DE 102005052752 A1 5/2007
WO 91/05261 A1 4/1991
WO 99/00855 1/1999

(56) References Cited

FOREIGN PATENT DOCUMENTS

| | | | |
|---|---|---|---|
| WO | 2004/057319 | A1 | 7/2004 |
| WO | 2008/019693 | A2 | 2/2008 |
| WO | 2011/102065 | A1 | 8/2011 |
| WO | 2012054758 | A2 | 4/2012 |
| WO | 2014012136 | A2 | 1/2014 |
| WO | 2014/143680 | A1 | 9/2014 |
| WO | 2014190240 | A1 | 11/2014 |
| WO | 2014190292 | A1 | 11/2014 |
| WO | 2016/044132 | A1 | 3/2016 |
| WO | 2016044055 | A1 | 3/2016 |

OTHER PUBLICATIONS

Chen et al., A pure shear mode ZnO film resonator for the detection of organophosphorous pesticides, Sensors and Actuators B: Chemical, Jun. 26, 2012; 171-172, 1081-6.

Gan et al., A Signal-Amplified Piezoelectric Sensor for the detection of hs-CRP Using HRP Doped Magnetic Core-Shell Fe3O4@SiO2@Au Nanostructures as Labels, 2012, Int. J. Electrochem, Sci, 7:11567-77.

Kokkonen et al, Measurement of Evanescent Wave Properties of a Bulk Acoustic wave Resonator, IEEE Transactions on Ultrasonics, Ferroelectrics, and Frequency Control, Mar. 2012; 59(3):557-59.

Lee et al, Highly sensitive biosensing using arrays of plasmonic Au nanodisks realized by nanoimprint lithography, Feb. 22, 2012, ACS Nano, 5(2):897-904.

Martin et al, Optimisation of the enzyme-based determination of hydrogen peroxide using the quartz crystal microbalance, Sep. 2002, Biosensors and Bioelectronic, 17(9) 735-39.

Patolsky et al, Precipitation of an insoluble produce on enzyme monolayer electrodes for biosensor applications: characterization by Faradaic impedance spectroscopy, cyclic voltammetry, and microgravimetric quartz crystal microbalance analyses, Aug. 1, 1999, Anal. Chem, 71(15):3171-80.

Tang et al., Enzymatically biocatalytic precipitates amplifies antibody-antigen interaction for super low level immunoassay: an investigation combined surface plasmon resonance with electrochemistry, Dec. 15, 2007, Biosensors and Bioelectronics, 23(5):668-74.

Wang et al., Label-free immunosensor based on micromachined bulk acoustic resonator for the detection of trace pesticide residues Sensors and Actuators B: Chemicals, Jan. 2014, 190:378-83. Epub Sep. 8, 2013.

Wingqvist et al., Immunosensor utilizing a shear mode thin film bulk acoustic sensor Sensors and Actuators B: Chemical Oct. 20, 2007, 127(1):248-52.

Waggoner et al., Atomic Layer Deposition Silicon Dioxide Films on Nanomechanical Silicon Nitride Resonators J Appl Phys, 2010; 107-114505, 5 pages.

Yang et al., Effects of Diffusion Boundary Layer on Reaction Kinetics of Immunoassay in a Biosensor J Appl Phys, Apr. 28, 2008, 10:084702, 10 pages.

* cited by examiner

TWO PART ASSEMBLY

CROSS-REFERENCE TO RELATED APPLICATIONS

This application is a continuation application claiming priority to U.S. application Ser. No. 17/014,694, filed on Sep. 8, 2020, now U.S. Pat. No. 11,933,793B2, which is a continuation of U.S. application Ser. No. 14/893,388, filed on Nov. 23, 2015, now abandoned, which is a U.S. National State Application of International Application Number PCT/US2014/039400, filed on May 23, 2014, now lapsed, which is based on and claims priority to U.S. Provisional Application No. 61/826,845, filed on May 23, 2013, now lapsed, each of which are hereby incorporated by reference in their entirety as if fully recited herein.

BACKGROUND AND SUMMARY OF THE INVENTION

There are numerous instruments and measurement techniques for diagnostic testing of materials related to medical, veterinary medical, environmental, biohazard, bioterrorism, agricultural commodity, and food safety. Diagnostic testing traditionally requires long response times to obtain meaningful data, involves expensive remote or cumbersome laboratory equipment, requires large sample size, utilizes multiple reagents, demands highly trained users, and can involve significant direct and indirect costs. For example, in both the human and veterinary diagnostic markets, most tests require that a sample be collected from a patient and then sent to a laboratory, where the results are not available for several hours or days. As a result, the caregiver must wait to treat the patient.

Point of use (or point of care when discussing human or veterinary medicine) solutions for diagnostic testing and analysis, although capable of solving most of the noted drawbacks, remain somewhat limited. Even some of the point of use solutions that are available are limited in sensitivity and reproducibility compared to in laboratory testing. There is also often significant direct costs to a user as there can be separate systems for each point of use test that is available.

Disclosed herein are devices that includes a first portion, the first portion including at least one fluidic pathway; a fluid actuator; and an introducer; a second portion, the second portion including at least one well, the well containing at least one material, wherein one of the first or second portion is moveable with respect to the other, the introducer is configured to obtain at least a portion of the material from the at least one well and deliver it to the fluidic pathway, and the fluid actuator is configured to move at least a portion of the material in the fluidic pathway.

Also disclosed are systems that include an assembly, the assembly including a first portion, the first portion including at least one fluidic pathway; a fluid actuator; an introducer; and a sensor positioned within the fluidic pathway; a second portion, the second portion including at least one well, the well containing at least one material, wherein one of the first or second portion is moveable with respect to the other, the introducer is configured to obtain at least a portion of the material from the at least one well and deliver it to the fluidic pathway, and the fluid actuator is configured to move at least a portion of the material in the fluidic pathway; and an external instrument, the external instrument configured to attain a signal from the sensor.

Also disclosed are methods that include steps of providing a first device, the first device including a first portion, the first portion including at least one fluidic pathway; a fluid actuator; an introducer; and a sensor positioned within the fluidic pathway; a second portion, the second portion including at least one well containing at least one material; a sample well; and an empty well, wherein one of the first or second portion is moveable with respect to the other, the introducer is configured to obtain at least a portion of the material from the at least one well and deliver it to the fluidic pathway, and the fluid actuator is configured to move at least a portion of the material in the fluidic pathway; placing a sample in the sample well; obtaining at least a portion of the at least one composition from the at least one well and depositing it in the fluidic pathway; obtaining at least a portion of the sample from the sample well and depositing it in the fluidic pathway; actuating fluid in the fluidic pathway so that at least a portion of the sample and the at least one composition reach the sensor; monitoring at least one signal from the sensor; and depositing at least some of the sample, at least one composition, or some combination thereof in the empty well.

These and various other features will be apparent from a reading of the following detailed description and related drawings.

Figure 1:
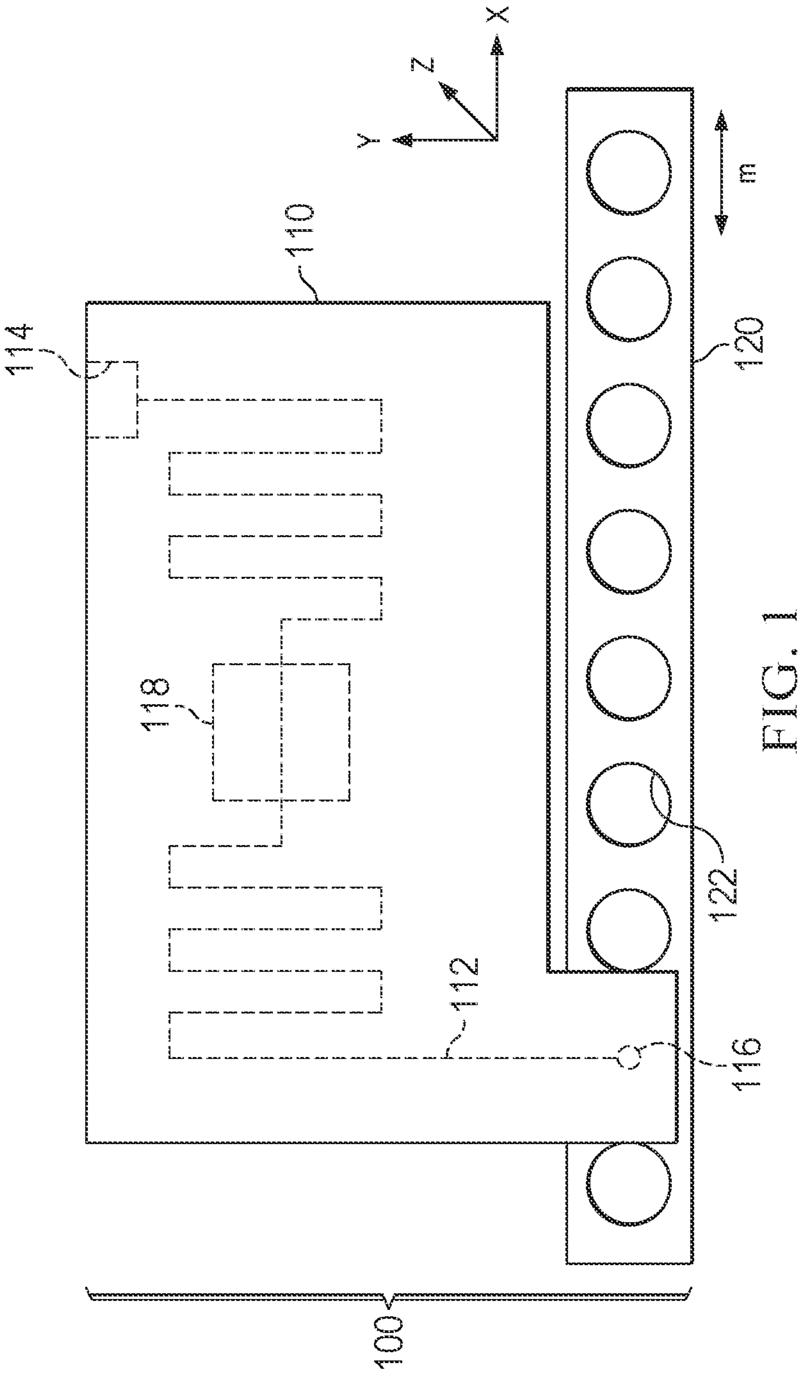
FIG. 1 is a schematic diagram illustrating an illustrative sensor assembly.

The drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION OF EXEMPLARY EMBODIMENT(S)

In the following detailed description several specific embodiments of compounds, compositions, products and methods are disclosed. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms “a”, “an”, and “the” encompass embodiments having plural referents, unless the content clearly dictates otherwise.

As used in this specification and the appended claims, the term “or” is generally employed in its sense including “and/or” unless the content clearly dictates otherwise. The term “and/or” means one or all of the listed elements or a combination of any two or more of the listed elements.

As used herein, “have”, “having”, “include”, “including”, “comprise”, “comprising” or the like are used in their open-ended sense, and generally mean “including, but not limited to”. It will be understood that “consisting essentially of”, “consisting of”, and the like are subsumed in “comprising” and the like. As used herein, “consisting essentially of,” as it relates to a composition, product, method or the like, means that the components of the composition, product, method or the like are limited to the enumerated components and any other components that do not materially affect the basic and novel characteristic(s) of the composition, product, method or the like.

The words “preferred” and “preferably” refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure, including the claims.

Also herein, the recitations of numerical ranges by endpoints include all numbers subsumed within that range (e.g., 1 to 5 includes 1, 1.5, 2, 2.75, 3, 3.80, 4, 5, etc. or 10 or less includes 10, 9.4, 7.6, 5, 4.3, 2.9, 1.62, 0.3, etc.). Where a range of values is “up to” a particular value, that value is included within the range.

Any direction referred to herein, such as “top,” “bottom,” “left,” “right,” “upper,” “lower,” and other directions and orientations are described herein for clarity in reference to the figures and are not to be limiting of an actual device or system or use of the device or system. Devices or systems as described herein may be used in a number of directions and orientations.

Disclosed devices can accommodate a large breadth of testing protocols without requiring the platform to be entirely redesigned. Disclosed devices may also provide for the use of the same configuration for different protocols, meaning that only the materials would need to be different to afford different protocols to be undertaken with the devices. This along with the option of not including valves in portions of the consumable device can make the devices very cost effective to manufacture. The devices may also offer enhanced performance through mixing because of the two-way flow that is afforded by the devices. The two-way flow can also allow spent sample and reagents to be re-deposited in the wells from which they came, thereby making the sensor assembly a contained system with respect to sample and reagents.

Assembly

Disclosed herein is an assembly. In some embodiments, assemblies can include a first portion and a second portion. The first and second portions can be configured to be assembled together to form an assembly. The first and second portions can be assembled together by a manufacturer, an assembler, an end-user, or any combination thereof. The assembly of the two portions can be facilitated by the shape of the two portions, components of at least one of the two portions that are designed to facilitate assembly, or some combination thereof. The two portions can be made of the same material(s) or different materials. In some embodiments the first portion and the second portion can be made of different materials, which because of the different purposes of the two portions, may be useful. The two portions of the assembly can be manufactured separately, in the same or different facilities; and/or can be packaged and/or sold separately or together.

At least one of the first and second portions is moveable with respect to the other. This implies that after the first and second portion are assembled to form the assembly, one portion is moveable with respect to the other. The portion that is moveable with respect to the other can be moveable in one or more directions or dimensions. Movement of one portion with respect to the other may offer advantages in that wells in the second portion (discussed below) can be randomly accessed by the first portion. The ability to randomly access the wells in the second portion can allow a large breadth of protocols to be accomplished without altering the configuration of the assembly itself. Other possible advantages provided by the movability of one portion with respect to the other portion are discussed throughout this disclosure.

FIG. 1 illustrates an illustrative embodiment of an assembly. This illustrative assembly 100 includes a first portion 110 and a second portion 120. This particular illustrative assembly 100 is configured to be assembled in a way that positions the second portion 120 below the first portion 110 in the z direction. In some embodiments, the second portion 120 is moveable with respect to the first portion 110. The second portion being moveable with respect to the first portion can imply that the second portion can move in at least one dimension (x, y, or z) with respect to the first portion, which is stationary. In some embodiments, the second portion can move along a straight line with respect to the first portion (for example, along the x dimension). The embodiment depicted in FIG. 1 shows such movement, with the second portion 120 moving in the x direction (as indicated by the arrow designated m). In some embodiments, the second portion can move along a straight line with respect to the first portion (for example along the x dimension) and can move up and down with respect to the first portion (for example along the z dimension). Such movement could be seen in the assembly 100 if the second portion 120 also moved in the z dimension.

In some embodiments, the second portion can move around a fixed point with respect to the first portion (for example in a plane defined by the x and y dimensions). The embodiment depicted in FIGS. 4A and 4B could have such movement, with the second portion 420 moving in a circular direction (as indicated by the arc designated $m_a$) around a fixed point with respect to the first portion 410. This movement could be described as rotational movement. In some embodiments, the second portion can move around a fixed point with respect to the first portion (for example in a plane defined by the x and y dimension) and can move up and down with respect to the first portion (for example along the z dimension). Such movement could be seen in the assembly 400 if the second portion 420 also moved in the z dimension.

First Portion

The first portion can include at least one fluidic pathway, a fluid actuator, and an introducer. Fluidic pathways can also be described as including a fluid channel. The illustrative first portion 110 illustrated in FIG. 1 includes a fluid channel 112, a fluid actuator 114, and an introducer 116. Generally, the fluid channel 112, the fluid actuator 114, and the introducer 116 are in fluid communication with one another. It can also be described that the fluid actuator 114, the introducer 116, and the fluid channel 112 are within, on, or are part of the fluidic pathway.

The fluidic pathway can have various configurations, and the examples depicted herein serve only as illustrative configurations. In some embodiments, the fluidic pathway does not include portions of the device that obtain the sample. In some embodiments, the fluidic pathway begins after a sample is contained in a well of the second portion. The fluidic pathway can be described as a transit path for fluids in the assembly. The fluidic pathway need not be fluidly connected at all times. For example, the fluidic pathway can include a portion of the device that can be (based may be moved into or out of the fluid pathway, by for example moving one portion with respect to another portion. The fluidic pathway can also be described as including any portion of the device accessible by the introducer, any portion of the device fluidly connected with any portion of the device accessible by the introducer, or some combination thereof. The fluidic pathway need not include only an actual volume that is connected. In some embodiments, a fluidic pathway can be entirely housed on a first portion, entirely housed on a second portion, or at least one portion of a fluidic pathway can exist on a first and at least one portion of a fluidic pathway can exist on a second portion. In some embodiments, a fluidic pathway can be one that is connected at all times and in some embodiments, one or more than one portion of a fluidic pathway can be at some times disconnected from the remainder of the fluidic pathway. In some embodiments, a fluidic pathway can include a fluid channel. In some embodiments, such a fluid channel can be a volume that is connected at all times. In some embodiments, such a fluid channel can be entirely housed on the first portion of an assembly. In some embodiments, such a fluid channel can be entirely housed on the first portion of an assembly can be a volume that is statically connected at all times. A fluid channel can refer to a physical channel on a first portion of an assembly.

In some embodiments, the fluidic pathway does not include valves. In some embodiments, the fluid channel does not include valves. In some embodiments, fluid can flow in either direction in the fluidic pathway (or in the fluid channel) even though there are no valves. Bi-directional flow is possible, even though there may be no valves in the fluidic pathway (or the fluid channel) because of the ability to randomly access wells (for example an empty well) in the second portion. More specifically, two directional flow can be accomplished by depositing liquid (in some embodiments all the liquid) in the fluidic pathway (or the fluid channel) in an empty well on the second portion by flowing the fluid in a first direction and then retrieving that liquid from that well and directing it in the fluidic pathway by flowing the fluid in a second direction (opposite to the first direction). Accomplishing two-way flow without the use of any valves can make disclosed assemblies more cost effective to manufacture and less prone to issues that may accompany the use of valves.

Fluidic pathways (and therefore fluid channels that are part of a fluidic pathway) can have access to a sample introduction pathway as well. The sample introduction pathway and the fluidic pathway need not be entirely located on or in the same portion. The sample introduction pathway can include one or more than one component that can function to get a sample into a well. The sample introduction pathway can be described as a transit path for the sample before it is in a well. The sample introduction pathway need not be fluidly connected at all times. For example, the sample introduction pathway can include a portion of the device that can be (based on for example movement of one portion with respect to the other portion) moved into or out of the sample introduction pathway.

The sample introduction pathway can include, for example a sample introduction chamber and one or more than one component to get a sample from the sample introduction chamber to a well (on the second portion, discussed below). In some embodiments the sample introduction pathway can include one or more than one irreversible valve. A valve or valves that may be in the sample introduction pathway can also be described as not including moving parts. In some embodiments the sample introduction chamber can be located on or in the first portion. The sample introduction pathway can for example include a valve(s), a filter(s), or some combination thereof. In some embodiments the sample introduction pathway can utilize the introducer portion of the first portion. In some embodiments the sample can be moved from a sample introduction chamber to a sample well on the second portion.

In some embodiments, a sample introduction pathway can be configured to introduce sample directly into a fluidic pathway or a fluid channel that is part of a fluidic pathway. In such embodiments, the sample introduction pathway would be configured to deposit a sample into the fluidic pathway without first depositing it into a sample well.

Such configurations could be especially useful or applicable to instances where the sample size is relatively small. In some embodiments, such configurations could be utilized for sample sizes of not greater than 100 μL, for example. An example of such a sample could include a quantity of blood obtained via a finger prick.

FIG. 1 shows a fluid channel 112 that is part of the fluidic pathway. The fluid channel 112 can be formed (i.e., top, bottom and sides) from more than one component or piece of the first portion. In some embodiments, the fluid channel 112 does not contain any fluid valves. Illustrative fluid channels can be described by their volumes, either by their total volumes or by the volume both before and after the sensor. In some embodiments, illustrative fluid channels can have volumes of 10 μL to 1000 μL in the region before the sensor and 10 μL to 1000 μL in the region after the sensor. In some embodiments, illustrative fluid channels can have volumes of 50 μL to 250 μL in the region before the sensor and 50 μL to 250 μL in the region after the sensor. In some embodiments, illustrative fluid channels can have volumes of 75 μL to 200 μL in the region before the sensor and 75 μL to 200 μL in the region after the sensor. In some embodiments, illustrative fluid channels can have volumes of 100

μL to 175 μL in the region before the sensor and 100 μL to 175 μL in the region after the sensor. It should also be understood that the volumes before and after the sensor need not be the same.

The first portion also includes a fluid actuator 114. Although fluid actuator 114 is depicted as being at one end of the fluid channel 112, it should be understood that a fluid actuator could be located at any point along the fluid channel 112, could be located at multiple points along the fluid channel 112, and/or could have multiple components at multiple points along the fluid channel 112. The fluid actuator 114 functions to move fluid along the fluid channel 112. It can also be described that the fluid actuator 114 functions to move fluid along, into, out of, within (or any combination thereof) the fluid channel 112.

The fluid actuator 114 can be as simple as a port or as complex as a pump or diaphragm. Ln some embodiments, the fluid actuator 114 can be a port at the end of the fluid channel 112 (for example such as that depicted in FIG. 1) that is in fluid communication with a pump located external to the first portion. In some embodiments, the fluid actuator 114 is a port that is in fluid communication with a pump that is located on or within an external instrument that is configured to control and/or manipulate the sensor assembly. In some embodiments, the fluid actuator 114 can be a port that is in fluid communication with an entire fluidic control system. Illustrative fluidic control systems can include a pump(s), diaphragm(s), valve(s), further fluid channel(s), reservoir(s), or some combination thereof. In some embodiments, at least portions of the illustrative fluidic control system can be located on or within an external instrument, the first portion of the sensor assembly, the second portion of the sensor assembly, or some combination thereof. In some embodiments, the fluid actuator 114 can include a diaphragm that is in fluid communication with some portion of a fluidic control system.

The first portion also includes an introducer 116. The introducer 116 is on, within, or fluidly attached to the fluid channel 112 and functions to access the wells of the second portion (discussed below). The function of the introducer 116 can also be described as being configured to obtain at least a portion of the contents of at least one well on the second portion. The introducer 116 can be described as being able to both puncture sealed wells of the second portion and access and obtain at least a portion of the material in the well. The introducer 116 can be actuated by an external instrument in order to access the wells. Such actuation can include movement in one or more than one dimension. For example, in the example depicted in FIG. 1, movement of the introducer 116 in the z direction could afford access to at least one well on the second portion.

In some embodiments, the introducer 116 can also be configured to introduce air into a well it has accessed. This may allow the introducer 116 to more reliably obtain material from the wells. This optional function of the introducer 116 can be realized by the particular design of the tip of the introducer, by puncturing the seal to the well at two (instead of one) points simultaneously, at different times in a specified order, or by combinations thereof. In some embodiments, the introducer 116 can be similar in shape and configuration to a pipette tip.

The introducer 116 can also be configured to both extract material from a well of the second portion and introduce material into a well of the second portion. In such embodiments, the external instrument, in some embodiments through control of a pump for example, can control whether the introducer 116 is extracting or introducing material from or into the well. Introducing material into a well can allow for storage of materials, while not requiring a user to have concerns about liquids spilling out of a used sensor assembly. Introducing material into a well can also provide a method of mixing. Introducing material into a well can also provide a method of storing an intermediate composition while another step of a protocol is being carried out.

In some embodiments, the first portion 110 can also include a sensor 118. A sensor in a first portion can be any type of sensor, for example it could be an optical sensor (using for example chemiluminescence or fluorescence), an electrochemical sensor, or a resonant sensor. In some embodiments, the sensor 118 can include at least one thin film resonator sensor, such as a thin film bulk acoustic resonator (TFBAR) sensor. A TFBAR sensor includes a piezoelectric layer, or piezoelectric substrate, and input and output transducer. TFBAR sensors are small sensors making the technology particularly suitable for use in handheld or portable devices.

Figure 2A:
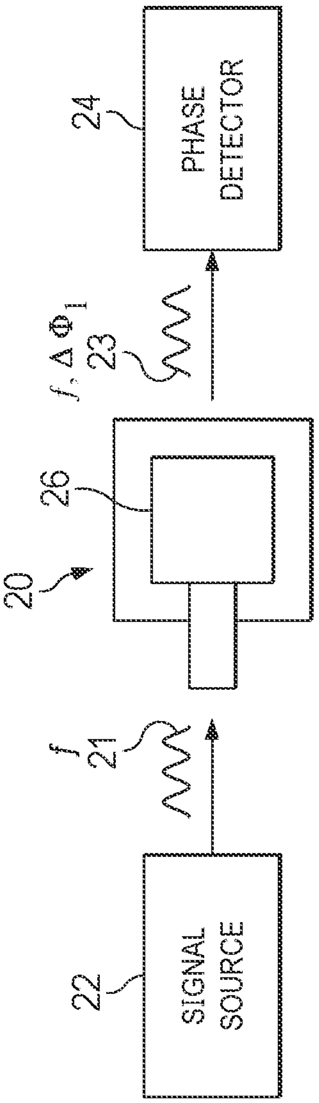
FIGS. 2A and 2B are schematic diagrams illustrating the operational principles of embodiments of thin film bulk acoustic resonator (TFBAR) sensing devices.
Figure 2B:
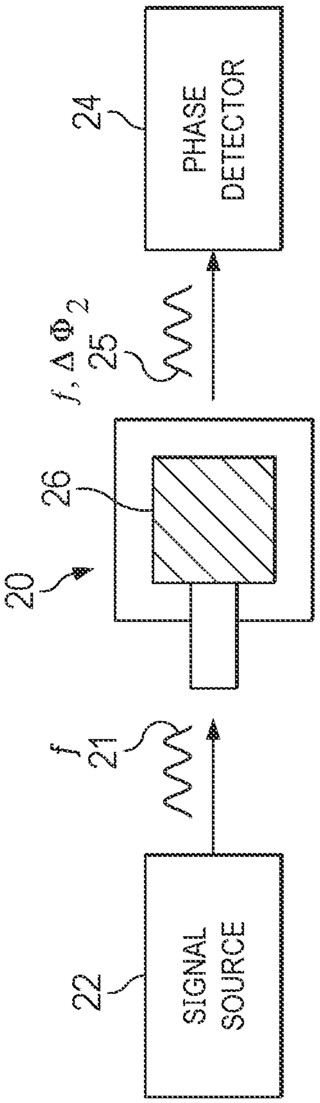

FIGS. 2A and 2B, general operating principles of a bulk-acoustic wave piezoelectric resonator 20 used as a sensor to detect an analyte are shown. The resonator 20 typically includes a planar layer of piezoelectric material bounded on opposite sides by two respective metal layers which form the electrodes of the resonator.

The two surfaces of the resonator are free to undergo vibrational movement when the resonator is driven by a signal within the resonance band of the resonator. When the resonator is used as a sensor, at least one of its surfaces is adapted to provide binding sites for the material being detected. The binding of the material on the surface of the resonator alters the resonant characteristics of the resonator, and the changes in the resonant characteristics are detected and interpreted to provide quantitative information regarding the material being detected.

By way of example, such quantitative information may be obtained by detecting a change in the insertion phase shift of the resonator caused by the binding of the material being detected on the surface of the resonator. Such sensors differ from those that operate the resonator as an oscillator and monitor changes in the oscillation frequency. Rather such sensors insert the resonator in the path of a signal of a pre-selected frequency and monitor the variation of the insertion phase shift caused by the binding of the material being detected on the resonator surface.

In more detail, FIG. 2A shows the resonator 20 before the material being detected is bound to its surface 26. The depicted resonator 20 is electrically coupled to a signal source 22, which provides an input electrical signal 21 having a frequency f within the resonance band of the resonator. The input electrical signal is coupled to the resonator 20 and transmitted through the resonator to provide an output electrical signal 23. The output electrical signal 23 is at the same frequency as the input signal 21, but differs in phase from the input signal by a phase shift $\Delta\phi_1$, which depends on the piezoelectric properties and physical dimensions of the resonator. The output signal 23 is coupled to a phase detector 24 which provides a phase signal related to the insertion phase shift.

FIG. 2B shows the sensing resonator 20 with the material being detected bound on its surface 26. The same input signal is coupled to the resonator 20. Because the resonant characteristics of the resonator are altered by the binding of the material as a perturbation, the insertion phase shift of the output signal 25 is changed to $\Delta\phi_2$. The change in insertion phase shift caused by the binding of the material is detected by the phase detector 24. The measured phase shift change is related to the amount of the material bound on the surface of the resonator.

In an alternative to measuring the insertion phase of the resonator, a directional coupler is added between the signal source and the resonator with the opposite electrode grounded. The phase detector is configured to measure the phase shift of the reflection coefficient as a result of material binding to the resonator surface.

Additional details regarding sensor devices and systems that may employ TFRs are described in, for example, U.S. Pat. No. 5,932,953 issued Aug. 3, 1999 to Drees et al., which patent is hereby incorporated herein by reference in its entirety to the extent that it does not conflict with the disclosure presented herein. Additionally, the sensor can utilize amplification schemes such as that disclosed in PCT Application No. PCT/US14/27743 filed on Mar. 14, 2014 entitled: Thin Film Bulk Acoustic Resonator With Signal Enhancement, the disclosure of which is incorporated herein by reference in its entirety to the extent that it does not conflict with the disclosure presented herein.

As discussed above, the binding sites for the material being detected can be utilized in combination with a resonant sensor. The binding sites for the material being detected could also be utilized with other types of sensors (examples of which were mentioned above and may include optical sensors such as chemiluminescent or fluorescent sensors and electrochemical sensors). In some embodiments the binding sites for the material being detected could also be utilized without an associated sensor in the fluidic pathway. In such embodiments, the fluidic pathway could be characterized as including a binding region (instead of a sensor that may include binding sites for the analyte of interest). The binding region could be configured with the binding sites being a material immobilized thereon. The immobilized material could be any material capable of interacting with an analyte of interest in such a way that would allow the analyte of interest to be analyzed. The immobilized material could include any component that selectively binds to the analyte of interest. By way of example, the immobilized material may be selected from the group consisting of nucleic acids, nucleotide, nucleoside, nucleic acids analogues such as PNA and LNA molecules, proteins, peptides, antibodies including IgA, IgG, IgM, IgE, lectins, enzymes, enzymes cofactors, enzyme substrates, enzymes inhibitors, receptors, ligands, kinases, Protein A, Poly U, Poly A, Poly lysine, triazine dye, boronic acid, thiol, heparin, polysaccharides, coomassie blue, azure A, metal-binding peptides, sugar, carbohydrate, chelating agents, prokaryotic cells and eukaryotic cells.

In some embodiments, the sensor 118 can be within or form part of the fluidic pathway. More specifically, in some embodiments, the sensor 118 can be within or form part of the fluid channel. For example, a portion of the fluidic pathway can be configured to exist within or form part of the fluidic pathway so that fluid in the fluidic pathway flows over the sensor. In some embodiments, the fluid in the fluidic pathway can travel completely around the sensor, and in other embodiments, the fluid in the fluidic pathway can travel around less than all surfaces of the sensor. In some embodiments, the fluid in the fluidic pathway can travel across the active region of the sensor. In some embodiments, the fluid in the fluidic pathway can flow over the piezoelectric layer of the sensor, which is coated with binding sites for an analyte of interest.

Figure 3:
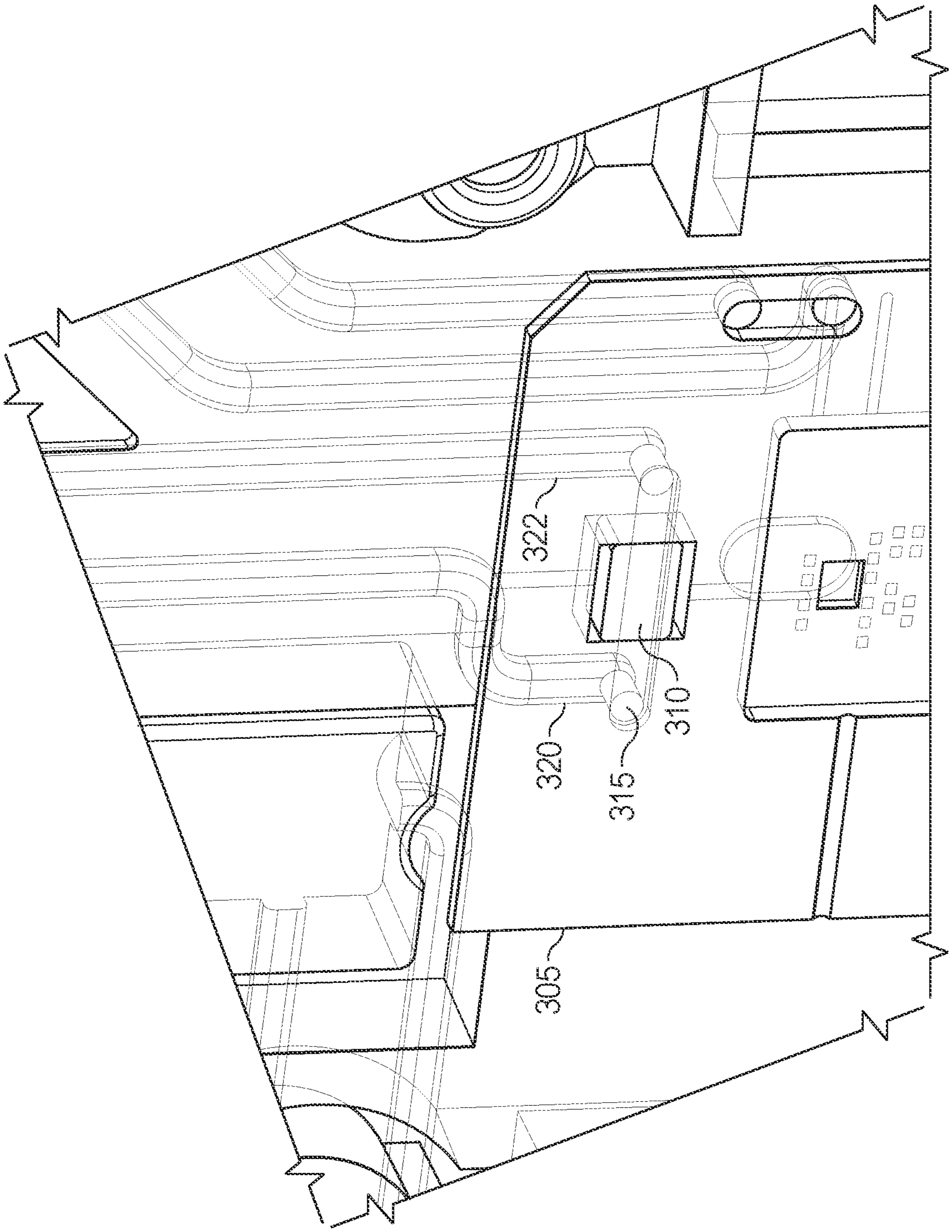
FIG. 3 is a perspective view of a portion of a sensor configured within a disclosed first portion.

In some embodiments, the sensor can be part of a sensor board. Illustrative sensor boards can include a hole, slot or pass through that allows the sensor to be part of the fluidic pathway. For example, the sensor or more specifically at least the piezoelectric layer of the sensor can be positioned within or over a slot or void in a sensor board. A specific example of such a configuration can be seen in FIG. 3. FIG. 3 shows a sensor board 305 that includes a sensor 310, the sensor can have characteristics such as those discussed above and includes a piezoelectric layer. Within the sensor board is a hole, void, or slot 315. The sensor 310 is positioned so that at least the piezoelectric layer of the sensor is within or positioned over the slot 315. The slot 315 is in fluid communication with the fluidic pathway. More specifically, a first sensor port 320 is fluidly connected to a first portion of the slot 315 and a second sensor port 322 is fluidly connected to a second portion of the slot 315. The first and second sensor ports 320 and 322 are part of the fluidic pathway present in a first portion of the sensor assembly. The configuration of the slot 315 and the piezoelectric layer of the sensor 310 with respect to the first and second sensor ports 320 and 322 render the piezoelectric layer of the sensor 310 part of the fluidic pathway or place it within the fluidic pathway. It should also be noted that other elements, such as for example, adhesives, films, etc. can be utilized in combination with the first and second ports 320 and 322, the sensor 310 and the slot 315 in order to form the fluidic pathway with the piezoelectric layer of the sensor 310 as part of or within the fluidic pathway.

Figure 8:
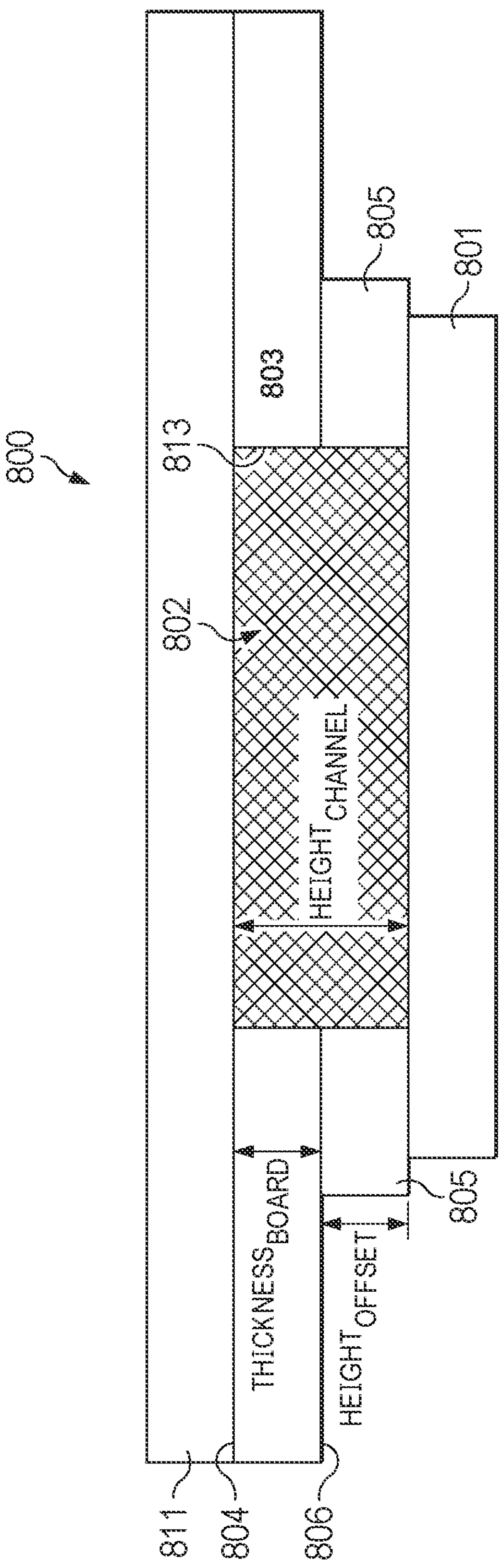
FIG. 8 shows a cross section of an illustrative channel that includes an associated sensor and electrical connection board.

FIG. 8 depicts an illustrative configuration of a sensor and a sensor board. The illustrative device 800 can include a sensor 801 and a board 803. The board 803 can also be referred to as an electrical connection board. The board 803 can be part of a flexible circuit board. The flexible circuit board can also be referred to as a printed circuit board (PCB). The flexible circuit board can include additional structures, components, devices, or some combination thereof not specifically discussed herein. The board 803 can be described as having a first surface 806 and an opposing second surface 804. Board 803 can also be characterized as having a thickness, given as $\text{thickness}_{board}$ in FIG. 8. The board 803 also includes a slot 802.

The sensor 801 can be any type of sensor. In some embodiments the sensor 801 can be an optical sensor (for example a chemiluminescent sensor or a fluorescent sensor) or a resonant sensor, for example. In some embodiments the sensor 801 can be a resonant sensor, such as a thin film bulk acoustic resonator (TFBAR) sensor. In some embodiments the sensor 801 can be in TFBAR sensor such as those discussed above. The sensor 801 is generally positioned on the board 803. The sensor 801 is positioned on the first surface 806 of the board. The sensor 801 spans the slot 802 of the board 803.

The illustrative device 800 also includes at least one, and in this embodiment two offsets 805. The at least one offset 805 can be described as being positioned between the sensor 801 and the first surface 806 of the board 803. FIG. 8 shows that the offset 805 can be described by the height or thickness thereof, $\text{height}_{offset}$.

The device 800 depicted in FIG. 8 also includes a sensor opposing member 811. The sensor opposing member 811 is positioned adjacent the second surface 804 of the board 803. The sensor opposing member 811, like the sensor 801 spans the slot 802 of the board 803. The sensor opposing member 811 can include numerous types of material. In some embodiments the sensor opposing member 811 can include polymeric materials. In some embodiments the sensor opposing member 811 can be described as flexible, and in some embodiments the sensor opposing member 811 can be described as rigid. In some embodiments the sensor opposing member 811 can include an adhesive property. In some embodiments the sensor opposing member 811 can include a polymeric material in combination with an adhesive material. In some embodiments the sensor opposing member 811 can be a pressure sensitive adhesive material. Illustrative pressure sensitive adhesive materials can include a polymeric film having an adhesive material coated on at least a portion thereof. Illustrative materials for the sensor opposing member 811 may be chosen based at least in part on the chemical nature thereof. For example the material could be chosen because it is relatively inert, it has relatively low levels of protein binding, or some combination thereof. As seen in FIG. 8, the combination of the board 803, the sensor 801, the offset 805, and the sensor opposing member 811 form a channel 813. The channel 813 in FIG. 8 is shown as dashed. The channel 813 may be part of or may be contained within the fluidic pathway discussed above. More particularly the channel 813 may be part of or may be contained within the analysis channel of the fluidic pathway discussed above.

The height of the channel 813, given as $height_{channel}$ is the sum of $height_{offse}t$ and $thickness_{board}$. In some embodiments $height_{channel}$ can be as small as 0.003 inches (about 0.07 millimeters (mm)) and in some embodiments as small as 0.008 inches (about 0.2 mm). In some embodiments $height_{channel}$ can be as large as 0.020 inches (about 0.5 mm), in some embodiments as large as 0.015 inches (about 0.4 mm), or in some embodiments as large as 0.012 inches (about 0.3 mm). A channel 813 that has a smaller height may be able to provide that a test could be run in a shorter period of time. The height of the channel 813 can affect the analysis time based at least in part on the linear velocity of the material going through the channel. The linear velocity of the solution relatively close to the surface where binding is to occur could be considered the most relevant factor. Because of the parabolic laminar flow profile, given the same average linear velocity, a shallower channel height will provide faster reaction times than a taller channel (up to the kinetic limit of the binding event). As the linear velocity increases the time necessary for an analysis that utilizes binding of two materials becomes less dependent on diffusion and more dependent on reaction kinetics. Because the diffusion is generally the rate limiting step, having a test that is more dependent on reaction kinetics provides a faster test. In some embodiments the channel 813 can be configured to provide a linear velocity therethrough that can be at least 0.1 mm/second, and in some embodiments at least 0.2 mm/second. In some embodiments the channel 813 can be configured to provide a linear velocity therethrough that can be not greater than 100 mm/second, in some embodiments not greater than 80 mm/second, and in some embodiments not greater than 20 mm/second.

The sensor 801 is electrically connected to the board 803. This allows the sensor 801 to be electronically monitored, controlled or some combination thereof via a device that could be electrically connected to the board 803. In the illustrative embodiment depicted in FIG. 8, the sensor 801 is electrically connected to the board 803 by the at least one offset 805. In the particular illustrative embodiment depicted in FIG. 8 two offsets 805 are included. In this particular embodiment, the offsets 805 can include electrically conductive material. For example the offsets 805 may be electrically conductive adhesive, or an electrically conductive metal or alloy (for example solder). In some embodiments the offsets 805 may be solder. In such embodiments the offsets 805 may be encapsulated with a secondary material. The secondary material may be chosen to, for example provides further structural stability to the channel, insulates the offsets 805, or some combination thereof. In some embodiments the secondary material may include an electrically insulating polymeric material, for example underfill.

In some embodiments the at least one offset 805 functions only as part of the channel 813 and is not electrically connect the sensor 801 to the board 803. In such embodiments, a separate structure can be utilized to electrically connect the sensor 801 to the board 803. For example, wire bonds may be utilized to electrically connect the sensor 801 to the board 803.

Second Portion

Disclosed assemblies also include a second portion. The second portion can include at least one well. FIG. 1 depicts an illustrative second portion 120 that includes a plurality of wells 122. Disclosed second portions of the assembly can include any number of wells. In some embodiments, a second portion can include at least one (1), at least three (3), or at least five (5) wells. In some embodiments, a second portion can include nine (9) wells with one being a sample well.

The wells within a second portion can be configured to contain the same or different volumes. In some embodiments, the wells can be of a size to contain at least 10 μL. In some embodiments, the wells can be of a size to contain from 50 μL to 150 μL, for example. In some embodiments, the wells can be of a size to contain about 100 μL for example. In some embodiments, the wells can have a total volume that is more than the quantity which they are designed to hold. For example, a well can have a total volume that is 200 μL in order to house a volume of 100 μL. The wells can have various configurations, including for example corners, flat bottoms, and round bottoms. The wells can have various shapes, for example, they can be cylindrical, or spherical, hexagonal, or otherwise.

Wells within a second portion can contain various materials or can be empty. In some embodiments, a second portion can include at least one well that is empty. In some embodiments a second portion can include at least one sample well. The sample well can generally be empty before the assembly is used. The sample well in such embodiments can be utilized to hold at least a portion of the sample transferred from a sample introduction chamber via the sample introduction pathway. In some embodiments, the sample well can include one or more than one materials, which the sample will be combined with upon introduction into the sample well.

Materials contained within wells can be liquid or solid. Materials contained within wells can also be referred to as reagents, diluents, wash solutions, buffer solutions, or other such terms. In some embodiments, material within a well can be a single material that is a liquid at room temperature, a solution containing more than one material, or a dispersion containing one material dispersed in another. In some embodiments, material within a well can be a solid. The material within an individual well can be independently selected with respect to materials in other wells. In some embodiments, the materials within a well are selected to carry out a particular testing protocol.

Figure 4A:
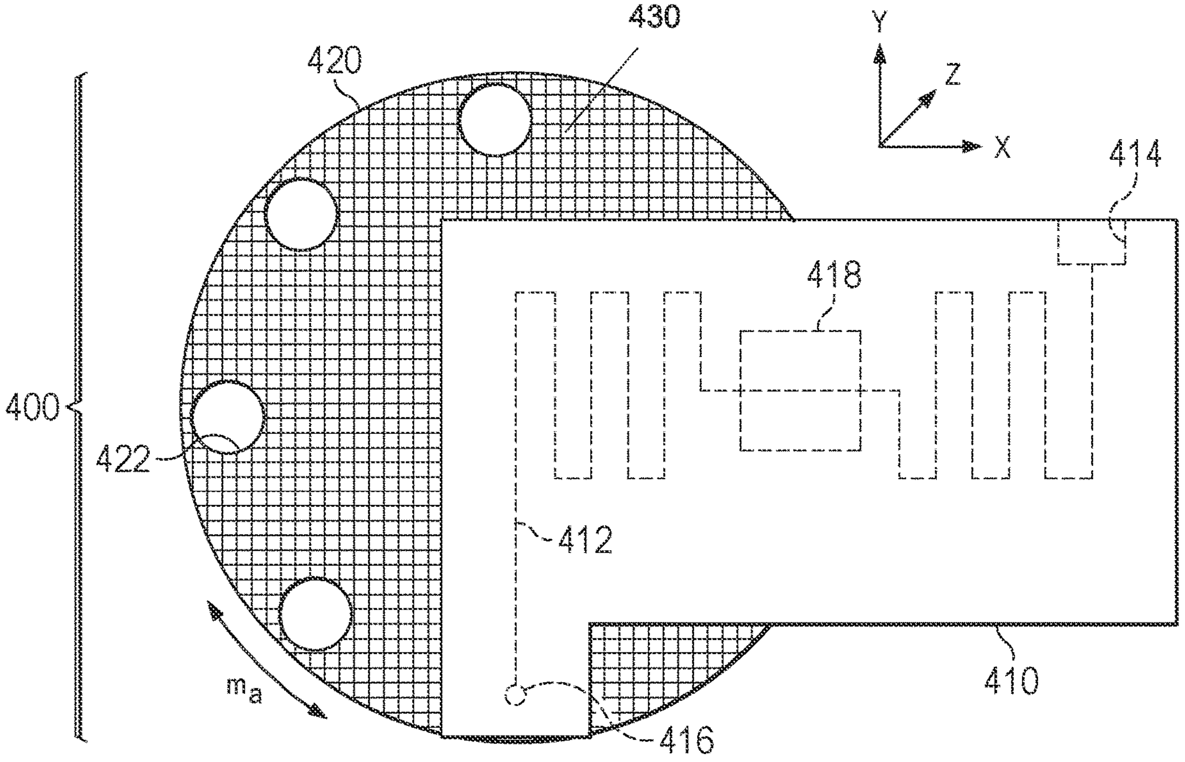
FIGS. 4A and 4B are a top-down view (FIG. 4A) and a cross section view (FIG. 4B) of a disclosed sensor assembly.
Figure 4B:
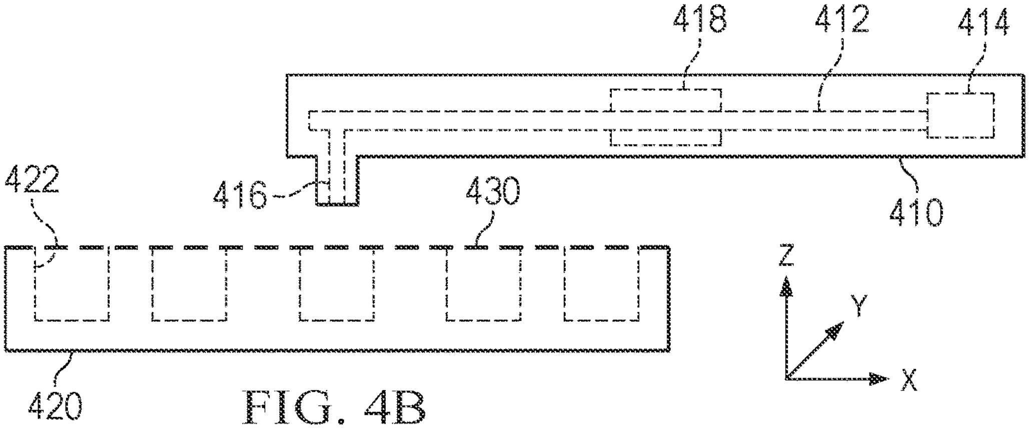

The second portion can also include a seal. Generally, the seal functions to contain the materials within the wells. In some embodiments, the seal can be a unitary clement, while in some embodiments, the seal can be made up of more than one element. For example, with reference to FIG. 1, in some embodiments, a single element could cover all of the wells 122. While in some other embodiments, each well 122 could be covered by an individual element, with all of the elements making up the seal. An exemplary seal is illustrated in FIGS. 4A and 4B. FIGS. 4A and 4B shows the seal 430 which is illustrated as the dashed line that covers the entire surface of the second portion 420. In other embodiments, not depicted herein, only the wells 422 of the second portion 420 could be covered with individual elements, the entirety of which can be considered as making up the seal.

The seal can be made of any material that can function to maintain the contents of the wells within the wells, but also allow the introducer 416 (in FIGS. 4A and 4B) access to the materials in the wells. Illustrative materials can include, for example, a foil, such as a metallic foil which can be sealed to the second portion (or portions thereof) via an adhesive or heat sealing; plastic films; or other such materials. In some embodiments, the seal is made of a metallic foil and covers the entirety of the second portion.

The second portion can also include a way of introducing a sample either directly or indirectly from a user. For example, in some embodiments, a second portion can include an empty well, whose seal can be pierced (if it is sealed) by a portion of a disclosed assembly or a user to introduce a sample to be tested by the sensor assembly. This well can be referred to as the sample well. In some embodiments, the sample well is not covered by the seal. In some embodiments where the sample is introduced directly to the second portion by a user it can be added to the sample well via a syringe, a pipette, or other similar instruments. In some embodiments, the sample can be added to a sample well via, for example a sample introduction pathway.

External Instrument

Disclosed assemblies can be utilized in combination with an external instrument. Illustrative external instruments can be bench top type and sized instruments, small hand-held type and sized instruments, or anything in between for example. In some embodiments, the external instrument can be a hand-held type instrument that is configured and designed for disclosed assemblies to be controlled and interrogated thereby. In some embodiments, the hand-held type external instrument can be configured to work with multiple assemblies (in some embodiments, assemblies that differ based on containing at least one different material in one well) that are designed for running multiple different analyses.

Such external instruments can be configured to control various features of the assembly. For example, an external instrument can be configured to be in fluid communication with the fluid actuator of the first portion of the assembly. The external instrument can then control fluid flow within the fluidic pathway. The external instrument can include a pump (or pumps), such as a syringe pump, piston pump, a screw pump, a peristaltic pump, a diaphragm pump, a solenoid pump, or similar devices. The external instrument can also include one or more other fluid path components, for example valves, couplers, etc. The external instrument can also include a control assembly for controlling the pump(s), valves, and other fluid path components. The external instrument can also be configured to control the movement of one of the portions of the assembly with respect to the other portion. The external instrument can include mechanisms for actuating one of the portions with respect to the other (for example the second portion with respect to the first portion) and control circuitry for controlling the mechanisms for actuating, for example. The external instrument can also include an electrical connection(s) for the sensor, hardware and software for monitoring the sensor, or combinations thereof.

It should also be noted that in some embodiments, the components noted above as being located within the external instrument: pump(s), other fluidic pathway components, control assemblies for controlling the fluidic pathway, control assemblies for controlling the movement of one portion with respect to the other portion, electrical connection(s); other components not discussed herein; or any combination thereof, can be located within the sensor assembly, for example within or on the first portion.

Disclosed fluidic pathways can allow for two-way flow of material within the fluidic pathway. Two-way flow may be enabled and/or enhanced by a number of features of the sensor assembly and/or the external instrument. For example, a pump within the external instrument can either be bi-directional or two pumps can be included. For example, the ability to randomly access the wells in the second portion can allow material to be accessed and returned. For example, an empty well can afford additional optional volume within the fluidic pathway (via access by the introducer) for permanent or temporary storage of material. For example, the fluidic pathway may have sufficient volume on both sides of the sensor to allow flow of the material across the sensor in both directions.

Two-way flow can enable mixing of various materials. For example, the sample can be aspirated from the sample well (flow away from the second portion), the second portion can be moved with respect to the first portion to place a different well beneath the introducer, and then the sample can be delivered to the well (flow towards the second portion). Two-way flow can also accomplish thorough mixing of one material (or solution) with another material (or solution). This could be accomplished, for example, by aspirating the contents of a well out of the well and then returning it to the well. The act of returning the contents to the well from the introducer will effectuate mixing. There are numerous other examples of instances where two-way flow could be advantageous, for example for diluting, reacting etc. Two-way flow can also be advantageous for allowing the sample to interact with the sensor. For example, the sample (once it has been diluted, for example and/or filtered, reacted, etc.) can be moved across the sensor in a first direction and then flow can be reversed so the sample is moved across the sensor in the opposite direction. Two-way flow can also allow limited sample volumes to be run across the sensor at fast flow rates for an extended period of time.

Disclosed herein are methods of mixing. Disclosed methods can utilize assemblies such as those discussed above. Disclosed methods can include a step of placing a sample in a sample introduction chamber. The sample introduction chamber can be on the first portion or the second portion. In some embodiments, the sample introduction chamber is on the first portion and this step transfers the sample from the sample introduction chamber on the first portion to a sample well (which may or may not be empty before use) on the second portion. In some embodiments, this step can be accomplished by using a sample introduction pathway as described above.

A next step in illustrative methods includes obtaining at least a portion of a material from a well on the second portion and depositing that material in the fluidic pathway. This step can be accomplished by using the introducer. The introducer can be controlled, via an external instrument for example, to access the well containing the material and deposit it in the fluidic pathway. The material obtained in this step may depend at least in part on the particular analysis being accomplished.

A next step in illustrative methods includes obtaining at least a portion of the sample from the sample well on the second portion and depositing that material in the fluidic pathway. This step can be accomplished by using the introducer. The introducer can be controlled, via an external instrument for example, to access the sample well and deposit it in the fluidic pathway. It should be noted that this step need not transfer all of the sample from the sample well into the fluidic pathway.

A next step in illustrative methods includes actuating fluid in the fluidic pathway. The fluid in the fluidic pathway is actuated in order to mix the sample with the material from the well. More specifically, the step can be accomplished by placing at least a portion of the sample and the material from the well in a third well on the second portion. This third well may be empty before the sample and the material is placed therein. The act of placing the material and the sample in the third well will afford mixing of the sample and the material.

Optionally after the sample and the material are placed in the third well, the mixed composition (containing the sample and the material upon mixing) can be taken up from the third well. Redepositing this material back in the third well (for example) can effectuate mixing. The steps of obtaining the composition and re-depositing it back in the well can be repeated any number of times. In some embodiments it can be repeated twice. In some embodiments it can be repeated at least two times.

A next step in illustrative methods includes actuating fluid in the fluidic pathway so that fluid reaches the sensor. This step can be accomplished via the fluid actuator on the first portion. More specifically, this step could be accomplished by a pump, for example located on an external instrument in fluid communication with the fluid actuator on the first portion. A next step includes monitoring at least one signal from the sensor. This step can be accomplished via an external instrument as discussed above. In some embodiments the step of actuating the fluid in the fluidic pathway so that the fluid reaches the sensor can be accomplished by reversing the direction of flow in the fluidic pathway at least once. In some embodiments the direction of flow can be reversed at least two times.

A next step in the illustrative methods includes depositing at least some of the fluid in the fluidic pathway into the second portion of the assembly. More specifically, at least some of the fluid from the fluidic pathway could be placed in a well in the second portion of the assembly. In such embodiments the well that is utilized may be one that was empty before the method was carried out, one that originally contained a material, or the sample well.

Disclosed assemblies can offer the advantage of being able to randomly access the wells within the second portion. Random access of the wells may be enabled and/or enhanced by the ability to move one of first or second portion with respect to the other. This allows the introducer to access any of the wells at any time. More specifically, the ability to randomly access the wells may be enabled and/or enhanced by at least two-dimensional movement of one portion with respect to the other portion. In some examples, the ability to randomly access the wells may be enabled and/or enhanced by three-dimensional movement of one portion with respect to the other portion. An example of this can be seen in FIGS. 4A and 4B, which shows movement of the second portion with respect to the first portion in the x, y, and z directions. This particular embodiment moves the second portion around a fixed point and also moves it up and down in the z direction.

Random access to the wells can enable access to any material present in the second portion at any time, not in a sequential manner for example. This can afford more flexibility in the variety of analyses that could be undertaken with the disclosed assemblies. Disclosed assemblies can therefore accommodate a large breadth of protocols and eliminate technological hurdles that existed in previous consumable designs. Previously utilized devices could be quite complex when multiple sample steps were integrated into the devices. Furthermore, slight changes in the protocol could potentially require a complete re-design of previously utilized devices. The ability to randomly access the wells provides a device that can overcome these and other drawbacks of previously utilized devices by providing an assembly that can accommodate variably different protocol configurations while simultaneously removing somewhat cumbersome constraints on the protocols being used.

Random access to wells can also offer different methods of mixing materials by adding a material to a well from another well, mixing in the well and then removing the mixed solution. Random access to wells can also allow the material to be returned to an already accessed well, an intentionally empty well, or both. This can afford an assembly that can function to contain all liquid material once the test is complete. Such a characteristic could be relevant from a safety and/or cleanliness standpoint.

As noted above, the second portion, which is entirely separate from the first portion until the assembly is put together, includes all of the materials necessary to run a protocol. In some embodiments, the second portion can include all non-bound materials (e.g., the binding material present in the fluidic pathway) necessary to run a protocol. In some embodiments, the first portion does not include any reagents or materials that are not bound to a surface. Because all of the non-bound materials are located on the second portion, the assembly can offer an analysis platform that may be relatively easy to utilize and/or modify for numerous different analyses. For example, if a different protocol is desired, the second portion merely needs to have the appropriate materials contained within the wells. The control assemblies for movement of one portion with respect to the other and the fluidic pathway (whether within an external instrument, the first portion, or some combination thereof) can then be configured to run the protocol with the different materials (reagents) being accessed from the second portion. Manufacturing efficiencies could be gained by being able to manufacture the first portion including the sensor without the need to load any materials (such as liquids, for example) on or into the first portion.

In some embodiments, an entirely different protocol can be undertaken using disclosed assemblies merely by changing one or more materials within the wells of the second portion. This can make such disclosed assemblies more commercially viable because the manufacture of the first portion need not change at all for different analyses. Furthermore, the manufacture of the second portion need not change either, different materials simply need be deposited into the wells during the manufacture process. Because different molds, dies, fixtures, etc., would not need to be made to extend the assembly to different protocols, disclosed assemblies could be commercially more successful for use as a multiple platform analysis system. The ability to run a number of different protocols using virtually the same assembly, can make systems that include disclosed assemblies and external instruments equivalent in function to large automated systems that would likely be much more expensive for an end user. Likewise the "porting" of assays from such large automated systems to the disclosed assemblies could potentially be relatively straight forward.

In some embodiments, the assembly can be considered to be a consumable. A "consumable" as utilized herein implies that the particular component will be discarded after use. The more inexpensive a consumable assembly is to manufacture, the more likely it is to be commercially successful. In some embodiments, disclosed assemblies do not include any valves within the fluidic pathway. This can make them less expensive to manufacture, when compared with fluidic pathways including valves. Disclosed valve-less assemblies could therefore be more apt to be commercially successful because of lower costs of manufacture and higher reliability.

Systems

Disclosed assemblies can be used in combination with another instrument, for example external instruments. As such, systems are disclosed utilizing disclosed assemblies and external instruments. Characteristics of both the assemblies and systems that were described above are also applicable to instances in which they are contained within a system. Disclosed systems can be assembled, configured or used by an end user, for example.

Methods

Disclosed devices (assemblies) and systems can be utilized to carry out various disclosed methods. An illustrative method can include a number of steps. For example, disclosed methods can include a step or steps of placing a sample in the sample introduction chamber. Any suitable method for sample collection and introduction can be utilized. Suitable methods for collection and introduction may change based on the type of sample and the target analyte to be detected.

Disclosed methods can also include steps of obtaining materials (either reagents originally contained in the wells or sample deposited into the sample introduction chamber) from one or more wells. Generally, such steps can be carried out by moving the first or second portion with respect to the other and moving fluid into or within the fluidic pathway, or combinations thereof. More specifically, such steps could be accomplished by moving a second portion (for example) with respect to a first one (e.g., in two dimensions for example x and y or rotationally) to align the correct well with the introducer and then move the second portion (for example) with respect to the first portion in a third dimension (for example z) to pierce a seal (if present) and obtain material from the well. Such steps can be controlled by a control assembly (and related circuitry and hardware as necessary) in the external instrument, for example.

Disclosed methods can also include a step (or steps) of actuating fluid in the fluidic pathway. Such steps could include, for example moving fluid into or out of wells, moving fluid back and forth in the fluidic pathway, moving fluid across (one or both ways) the sensor, or combinations thereof. Such steps can be controlled by a control assembly (and related circuitry and hardware as necessary) in the external instrument, for example.

Disclosed methods can also include a step (or steps) of monitoring a least one signal from a sensor. The signal to be sensed would depend at least in part on the type of sensor. The signal to be sensed in embodiments where the sensor is a resonant sensor can include, for example frequency, phase, frequency change, phase change, or any combination thereof. Other signals, not discussed herein, can also be monitored. The signal to be sensed in embodiments where the sensor is an optical sensor can include, for example voltage (from an image sensor for example) or current (from a photodiode). In embodiments where the sensor is an electrochemical sensor, the signal can be current, potential, or both, for example. Such steps can be controlled by a control assembly (and related circuitry and hardware as necessary) in the external instrument, for example.

Disclosed methods can also include a step (or steps) of depositing material into a well. In some embodiments, material can be deposited into a well that was previously empty, or a well that previously had material therein. Such a step can be enabled and/or allowed by the ability to utilize two-way flow in the fluidic pathway and to randomly access the wells on the second portion. Depositing material into a well can allow the system to be one that keeps the sample (which could be considered dangerous) contained after the analysis has been carried out. This allows the user to dispose of the entire cartridge, simultaneously disposing of the spent sample and any reagents that were utilized. Such steps can be controlled by a control assembly (and related circuitry and hardware as necessary) in the external instrument, for example.

Uses

The devices, systems, and methods described herein may be employed to detect a target analyte in a sample. The devices may find use in numerous chemical, environmental, food safety, or medial applications. By way of example, a sample to be tested may be, or may be derived from blood, serum, plasma, cerebrospinal fluid, saliva, urine, and the like. Other test compositions that are not fluid compositions may be dissolved or suspended in an appropriate solution or solvent for analysis.

Non-limiting examples of target analytes include nucleic acids, proteins, peptides, antibodies, enzymes, carbohydrates, chemical compounds, or infectious species such as bacteria, fungi, protozoa, viruses, pesticides and the like. In certain applications, the target analyte is capable of binding more than one molecular recognition component.

The present disclosure is illustrated by the following examples. It is to be understood that the particular examples, assumptions, modeling, and procedures are to be interpreted broadly in accordance with the scope and spirit of the disclosure as set forth herein.

EXAMPLES

Example 1—Sensor Assembly Including Linear Second Portion

Figure 5A:
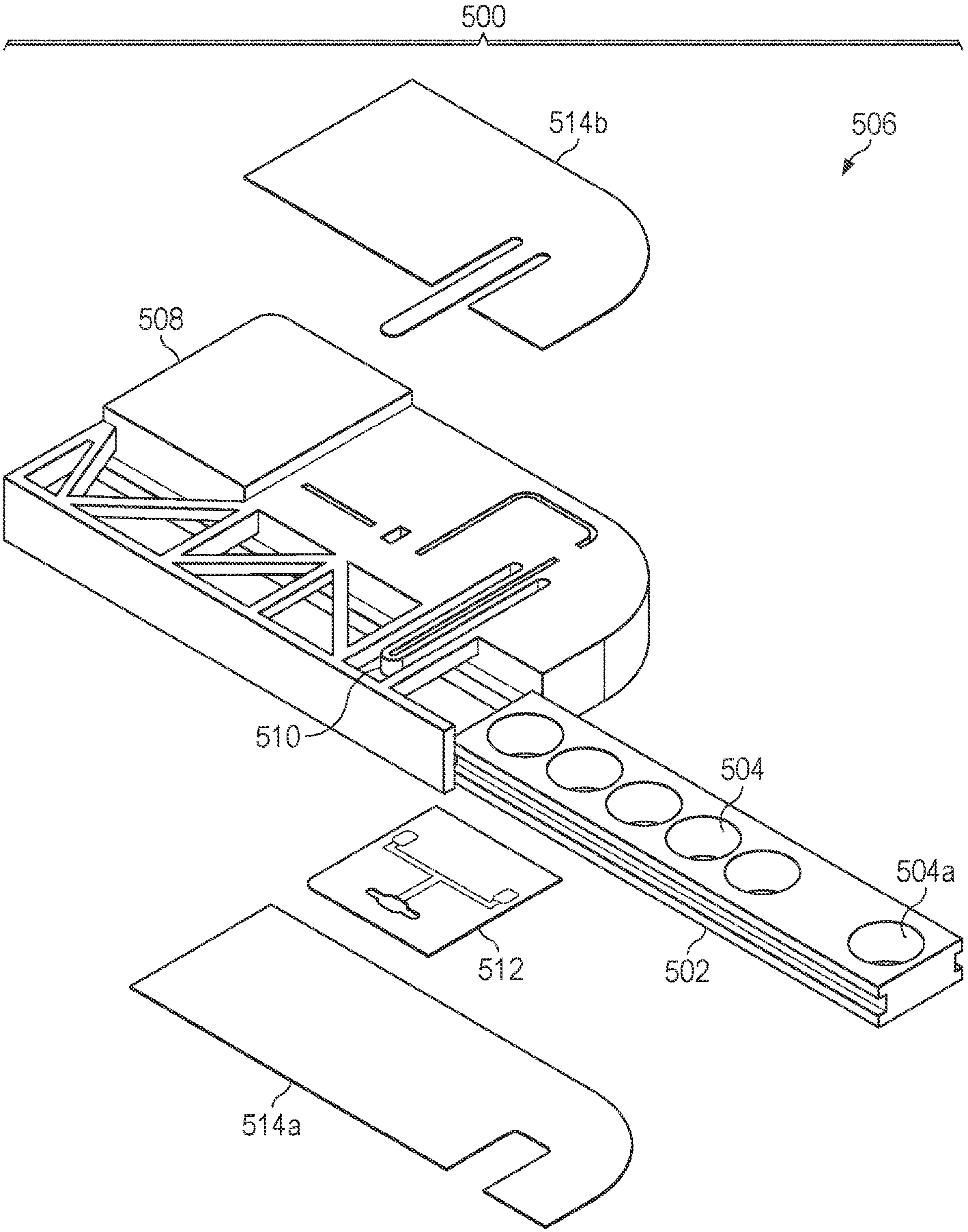
FIGS. 5A, 5B and 5C are an exploded view (FIG. 5A) and perspective views of a sensor assembly with the second portion at a first point with respect to the first portion (FIG. 5B) and at a second point with respect to the first portion (FIG. 5C).

An example of a specific disclosed embodiment is shown in FIG. 5A. The sensor assembly 500 includes a second portion 502 that includes six (6) wells (exemplified by well 504). In this particular embodiments, the second portion 502 is has a linear configuration. The remaining components shown in FIG. 5A make up the first portion 506 of the sensor assembly. Although not entirely visible in FIG. 5A, the cartridge 508, which is the external housing of the first portion 506, includes a fluidic pathway therein. The fluidic pathway terminates at one end at the introducer 510, which in this particular embodiment can function both as a tool to puncture the seals on the wells 504 and a pipette tip to access and aspirate materials from the wells. Also included within the first portion is the sensor 512. The sensor can be as described above and includes a piezoelectric layer that forms part of the fluidic pathway. The sensor 512 in this embodiment is housed on a sensor board, which includes a slot there through to enable the piezoelectric layer of the sensor to form part of the fluidic pathway. This particular illustrative sensor assembly is constructed using two die cut adhesive (in this particular example pressure sensitive adhesive) forms 514*a* and 514*b*.

Figure 5B:
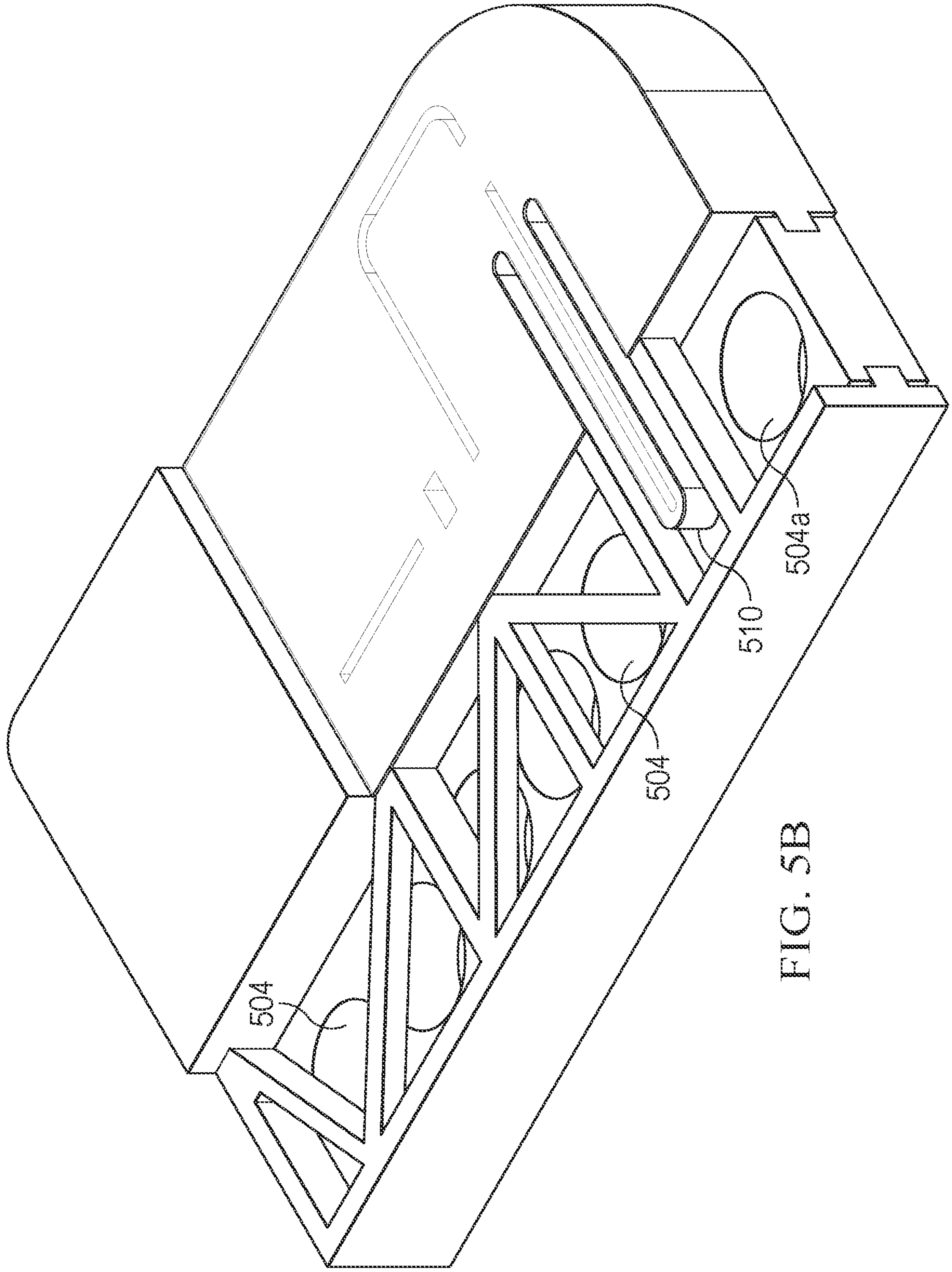
Figure 5C:
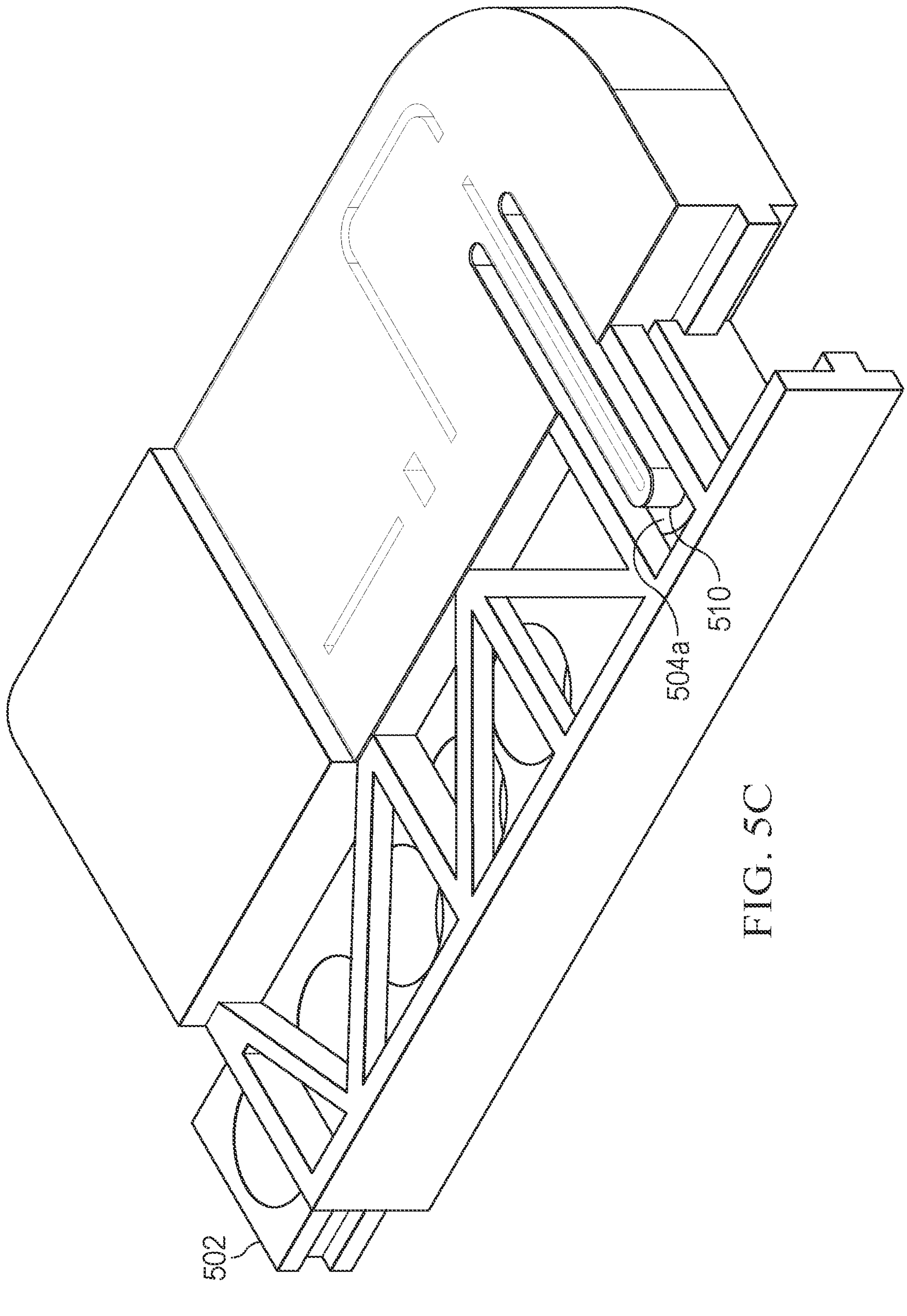

FIG. 5B shows the sensor assembly in an assembled form. As seen there, the second portion is completely inserted into a specifically designed track in the first portion and the wells 504 are ready to be accessed by the introducer 510. FIG. 5C shows the sensor assembly after the second portion 502 has been moved in a linear fashion so that the first well 504*a* (which is an arbitrary definition) of the second portion 502 can be accessed by the introducer 510.

The particular embodiment of a sensor assembly illustrated in FIGS. 5A, 5B, and 5C can be constructed using die cut adhesives and rapid cure UV-glue assembly that minimizes temperature rise. The channel height of the fluidic pathway above the sensor is defined by the thickness of the circuit board that the sensor is mounted to and the final distance below the board the sensor sits due to solder bump reflow. In some embodiments, the board thickness can be from 0.007"-0.008" and the sensor can typically sit 0.002" below the board surface. In such embodiments, the fluidic channel would be 0.009"-0.010" in height above the sensor surface. This height along with the channel width cutout in the board (referred to above as the slot) determines the linear velocity of the sample that flows across the sensor surface for a given flow rate. For detection of direct binding on a mass sensor, this linear velocity and channel height above the sensor determines the height of the depletion layer above the reaction surface for a given set of reaction kinetics. If the depletion layer is large, diffusion will limit the reaction rate and reaction kinetics cannot be accurately determined. As the linear velocity is increased, the depletion layer decreases and reaction kinetics can be accurately obtained. In point-of-care immunoassays for example, capture times are desired to be as fast as possible, therefore maintaining reaction rates at or near their kinetic limits is advantageous to minimize assay times even when not directly measuring mass binding such as in enzyme amplified systems.

Figure 6:
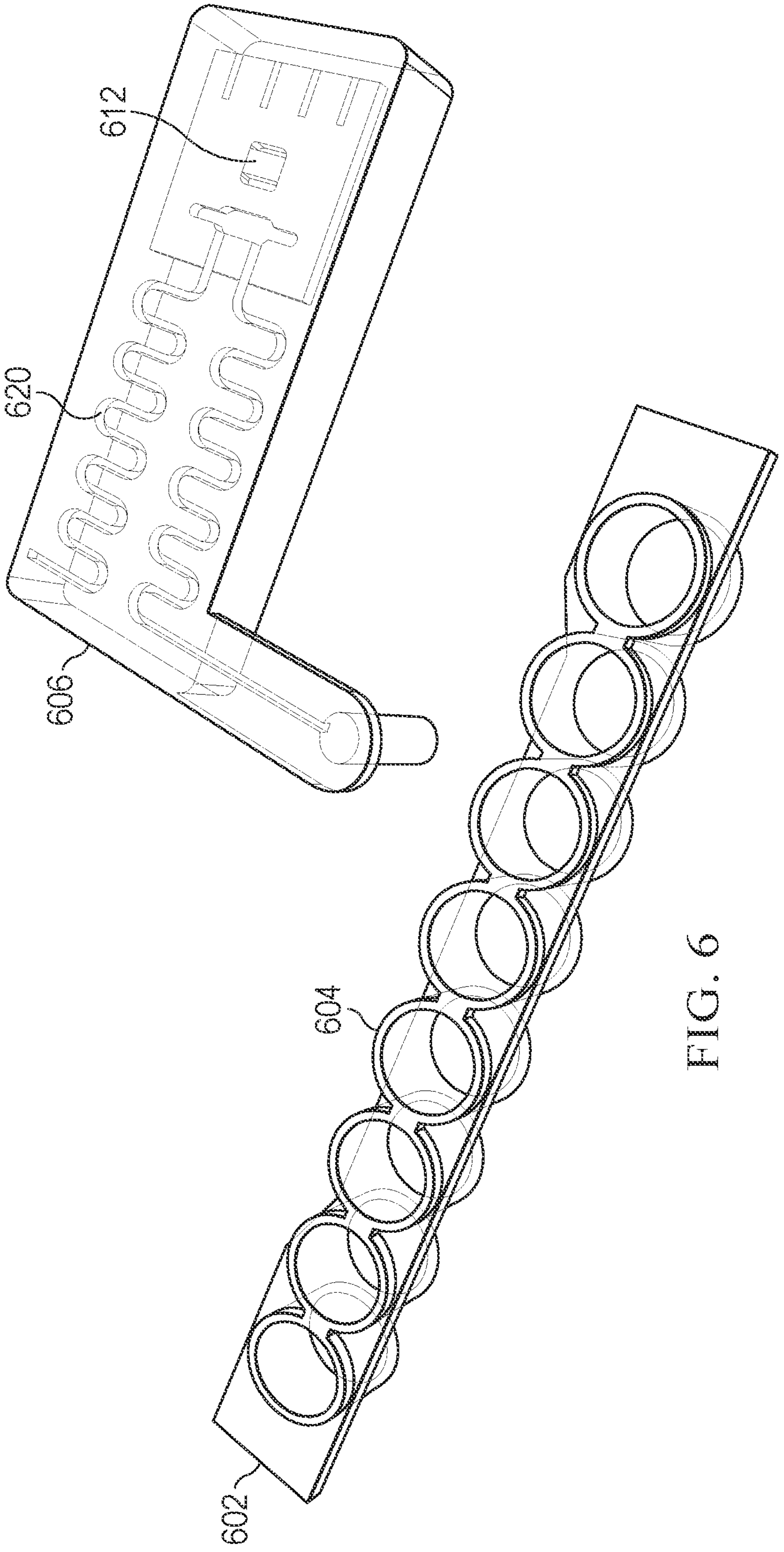
FIG. 6 is a photograph of an illustrative sensor assembly used to carry out Example 2A.

Example 2A—Use of Example I Sensor Assembly in a Two-Step Enzyme-Linked Immunoassay for TSH A two-step enzyme-linked immunoassay was carried out as follows using a sensor assembly as disclosed in FIG. 6. As seen in FIG. 6, the first portion 606 includes a fluidic pathway 620 and a sensor 612, and an introducer (not readily visible in FIG. 6). The fluidic pathway 620 seen in the first portion 606 had approximate volumes of 150 μL before and after the sensor in the fluidic pathway. The second portion 602 includes eight (8) wells, exemplified by well 604. In such an embodiment, the second portion 602 can be a commercially available eight (8) well strip with no seal that is available, for example from VWR International LLC (Radnor, PA) or Greiner Bio-One (Monroe, NC).

The two-step enzyme-linked immunoassay was to determine human thyroid stimulating hormone (TSH) in a human serum sample. The sensor was spotted with an anti-human TSH monoclonal antibody on the test resonator. The reference was spotted with a suitable isotype control antibody. The sensor was incubated overnight at 4° C. and 70% relative humidity (RH). The sensor was then rinsed, blocked for 30 minutes in a 1% bovine serum albumin (BSA) solution in phosphate buffered saline (PBS) buffer pH 7.2, rinsed, dried and coated with a 2% solution of sucrose. The sensor was then assembled into the first portion.

In the second portion, the reagent strip, well 1 contained 100 μL of sensor re-hydration buffer, well 2 contained 100 μL of a mixture of human serum and secondary antibody enzyme conjugate (Alkaline phosphatase), wells 3 to 5 contained 100 μL of wash buffer and well 6 contained 100 μL of enzyme substrate (i.e. 5-bromo-4-chloro-3'-indoly-phospate p-toluidine salt/nitro-blue tetrazolium chloride (BCIP/NBT)).

The first portion and second portion were placed into an external instrument. The external instrument indexed the second portion so that well 1 was below the introducer (the pipette tip). The instrument then actuated the reagent strip up to aspirate 80 μL of re-hydration buffer from well 1 into the first portion. The instrument then moved the re-hydration buffer over the sensor to remove the protein stabilizer from the sensor surface. The re-hydration buffer was then returned to well 1 of the second portion.

Next the instrument indexed the reagent strip so that well 2 was below the pipette tip. The reagent strip was then actuated up and 80 μL of serum conjugate mixture was aspirated into the first portion. The instrument then pumped the serum conjugate mixture across the sensor for a fixed reaction time between 1 and 10 minutes, in this example about four (4) minutes. At the completion of the reaction the mixture was then returned to well 2. The instrument then indexed the reagent strip so that well 3 was below the pipette tip and 80 μL of wash buffer was moved across the sensor for 30 seconds and returned to well 3. The wash sequence was then repeated for wells 4 and 5. Well 6 was then indexed below the pipette tip and 80 μL of substrate solution was moved across the sensor for a time between 30 and 120 seconds, in this example about 120 seconds, and then returned to well 6. Sensor response was read by the instrument throughout the procedure to monitor direct binding of the diluted sample to the sensor as well as measure the enzymatic precipitation on the sensor surface.

Example 2B—Use of Example 1 Sensor Assembly in a Two-Step Enzyme-Linked Immunoassay for TSH with Mixing The protocol from Example 2A can be carried out and if desired, the sample can be loaded into a well. Material to dilute the sample can be provided in a well, and upon dilution mixing can be effectuated by pipetting the mixture in and out of the well after the sample was added to the diluent (or vice versa). The mixture can be aspirated in and out the well from one (1) to about six (6) times.

Example 3—Sensor Assembly Including Circular Second Portion

Figure 7A:
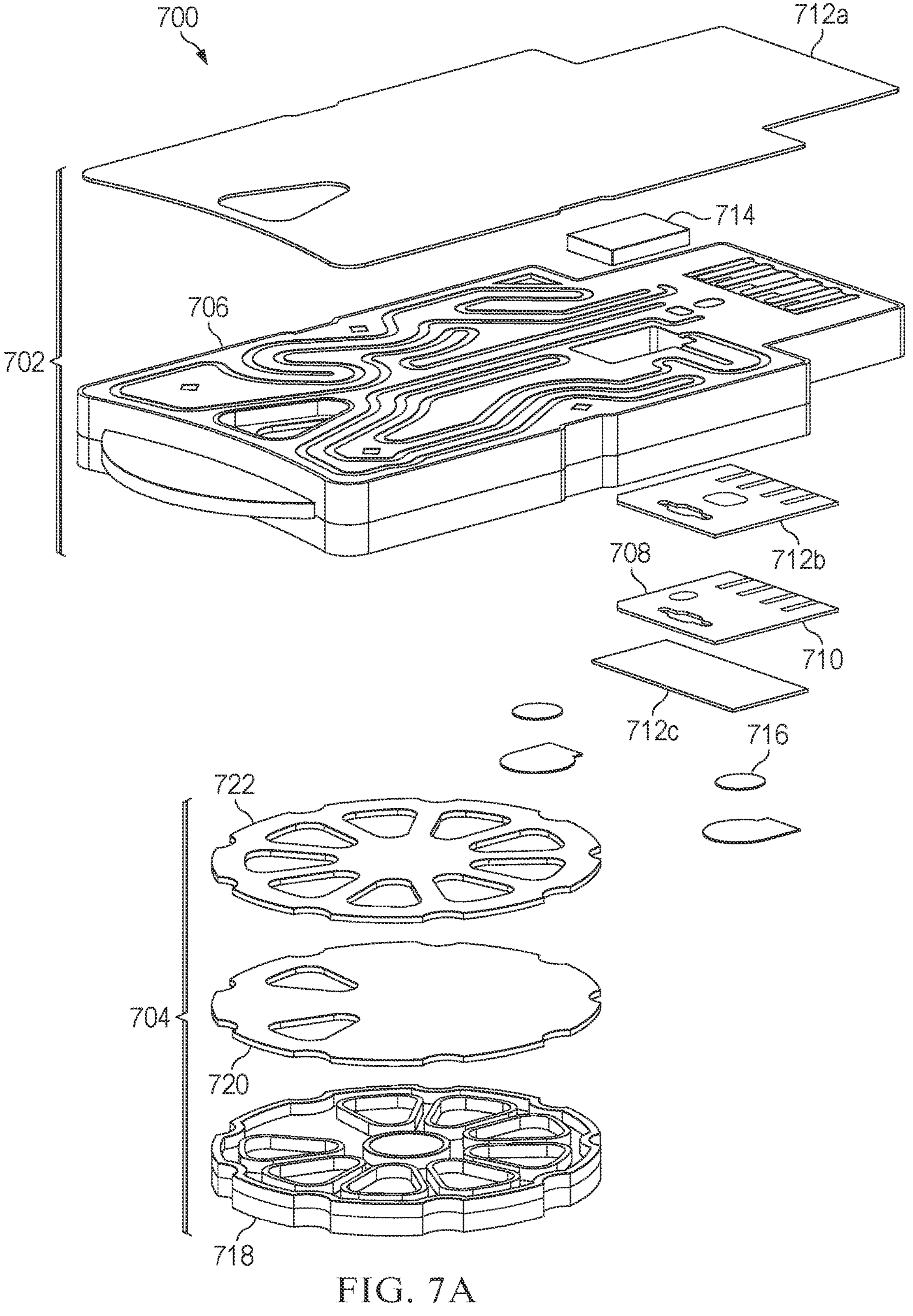
FIGS. 7A, 7B, 7C, 7D, 7E, 7F, and 7G are an exploded view (FIG. 7A), a cross sectional view of a portion including the introducer (FIG. 7B), a perspective view of a portion including the sensor (FIG. 7C), a bottom view of a portion (FIG. 7D), a perspective view of a cross section of a portion including the sensor (FIG. 7E), a bottom view of the entire (FIG. 7F) illustrative assembled sensor assembly, and a top view of the entire (FIG. 7G) illustrative assembled sensor assembly.

FIG. 7A shows an exploded view of an illustration of a specific embodiment of a sensor assembly that includes a circular second portion. The sensor assembly 700 includes a first portion 702 and a second portion 704. The first portion 702 includes a channel 706 and a sensor 708 on a sensor board 710. Although not necessarily easily visible in FIG. 7A, the sensor board 710 includes a slot in which at least the piezoelectric layer of the sensor 708 sits. The first portion 702 also includes three different adhesive films 712*a*, 712*b*, and 712*c*. The adhesive films 712*a*, 712*b*, and 712*c* along with the channel 706 and at least a portion of the sensor board 710 and sensor 708 form the fluidic pathway. This particular illustrative sensor assembly also includes a waste wick 714, which is within or in fluid communication with the fluidic pathway. The waste wick 714 can function to contain overflow fluid from the fluidic channel. This particular illustrative sensor assembly also includes at least one, and in this embodiment two hydrophobic vents 716. The hydrophobic vents 716 function to provide a liquid stop for use in metering and to prevent liquid ingress into the instrument when using an external pump.

The second portion 704 is circular and is configured to be rotated around a central point. The second portion 704 includes eight (8) wells (illustrated by well 718). The wells 718 in this illustrative embodiment have a teardrop shape. Shapes such as a teardrop shape may provide an advantageous use of space, but it should also be noted that other shapes, such as circular shapes for example could also be suitable. It should also be noted that there are portions of the housing of the second portion that do not include wells. The portion without a well can be utilized in order to have a position for the introducer upon assembly of the first and second portion. It is noted that the empty well for the introducer to be placed in upon initial assembly cannot be the sample introduction well, because it has to be accessible for introduction of the sample. It should also be noted that this function could be served by an additional empty well (instead of a void). In this particular embodiment, the wells are sealed with one portion or piece of material, a seal 720. In this illustrative embodiment, the seal 720 is made of a metal foil. This particular embodiment of the seal 720 includes two openings that are positioned over the voids. These openings can allow advantageous assembly with introducer placement. This particular embodiment of a sensor assembly also includes a gasket layer 722. The gasket layer 722 can be made of any material that is somewhat compliant (to allow for a gasket type of function), and in some embodiments, the gasket material does not absorb a sufficient amount of liquid. The gasket layer 722 can be advantageous because it can function to seal the wells once they have been punctured by the introducer. In some embodiments, the gasket layer 722 can be attached to (via adhesive for example), or formed integrally with the seal 720.

Figure 7B:
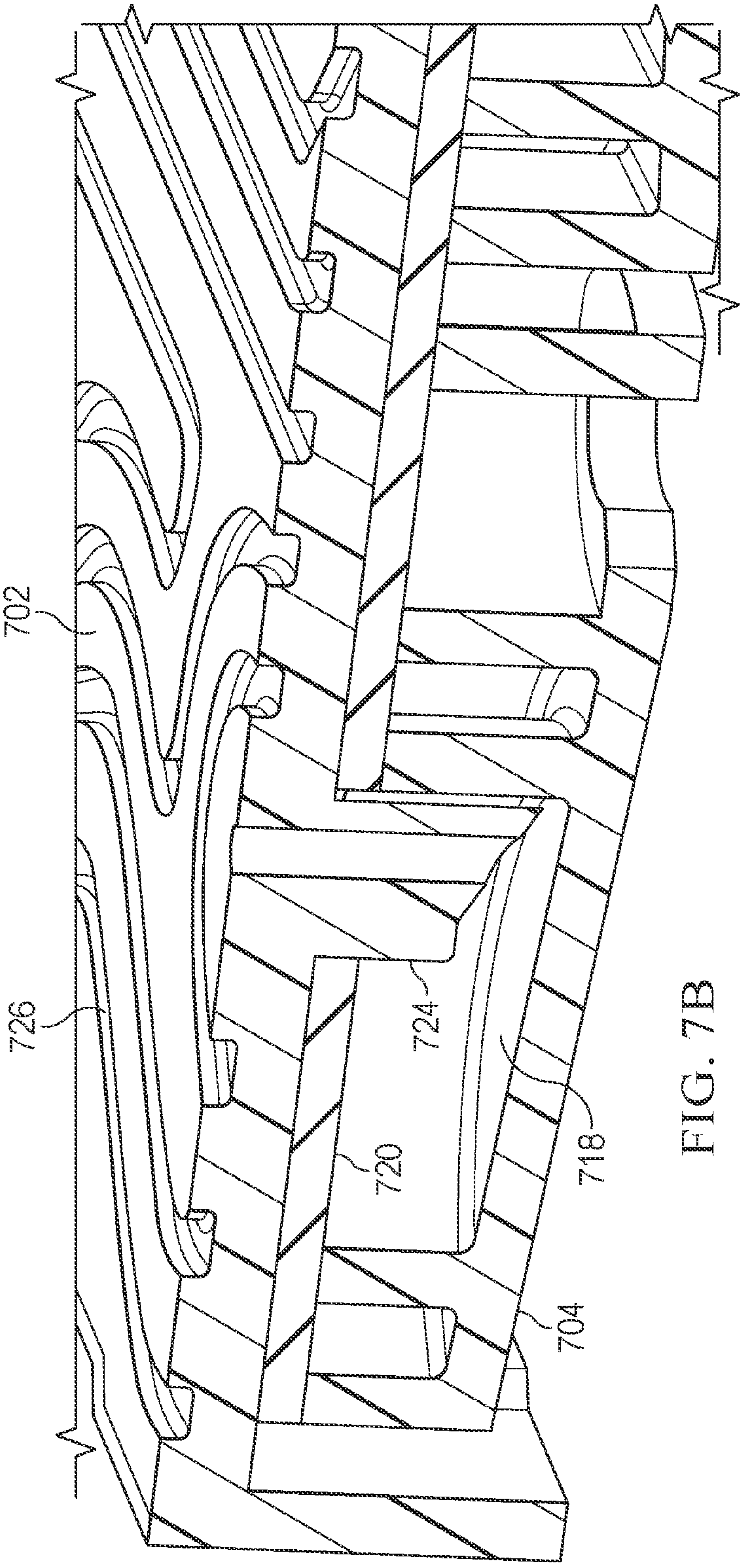
Figure 7C:
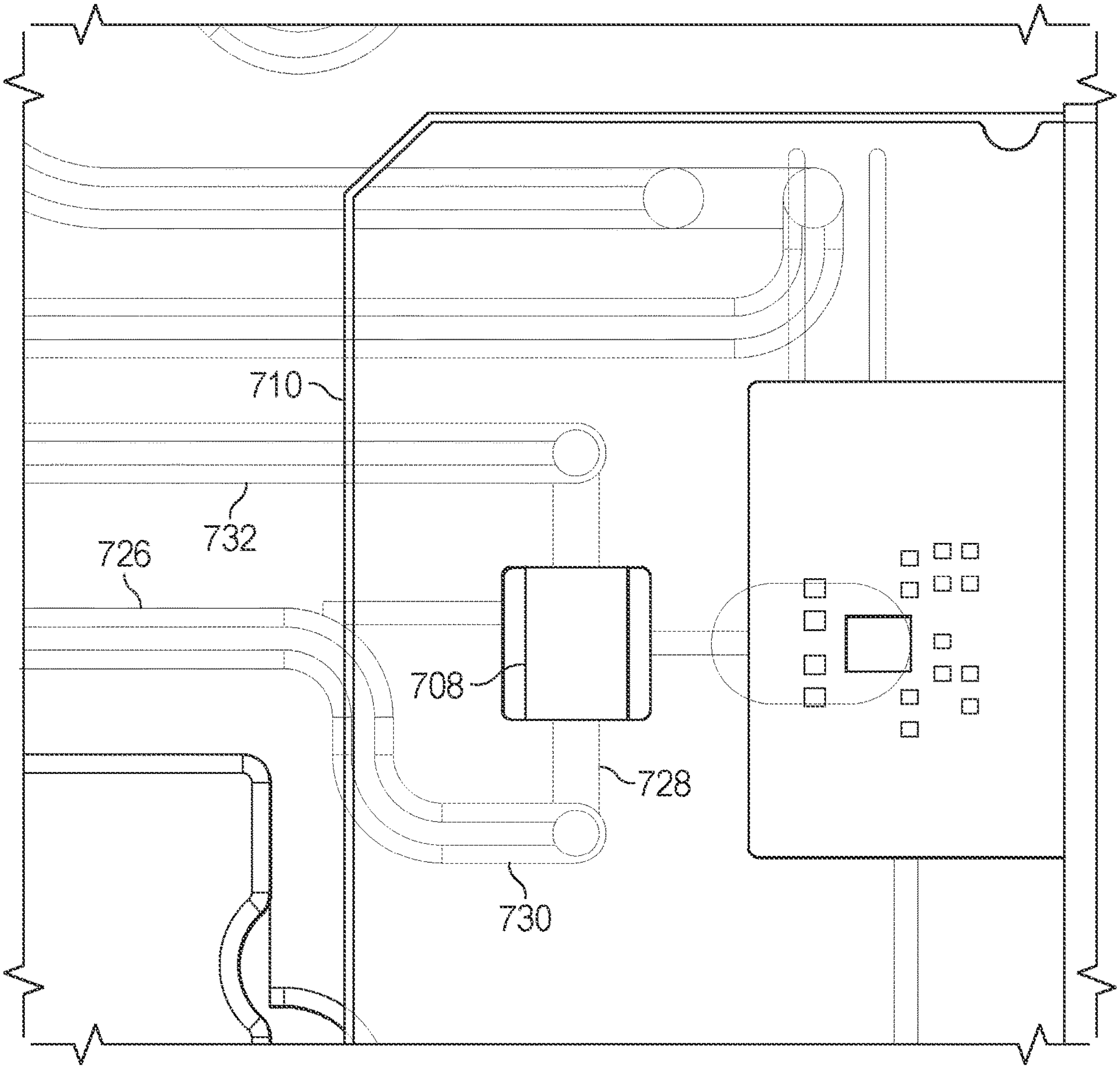
Figure 7D:
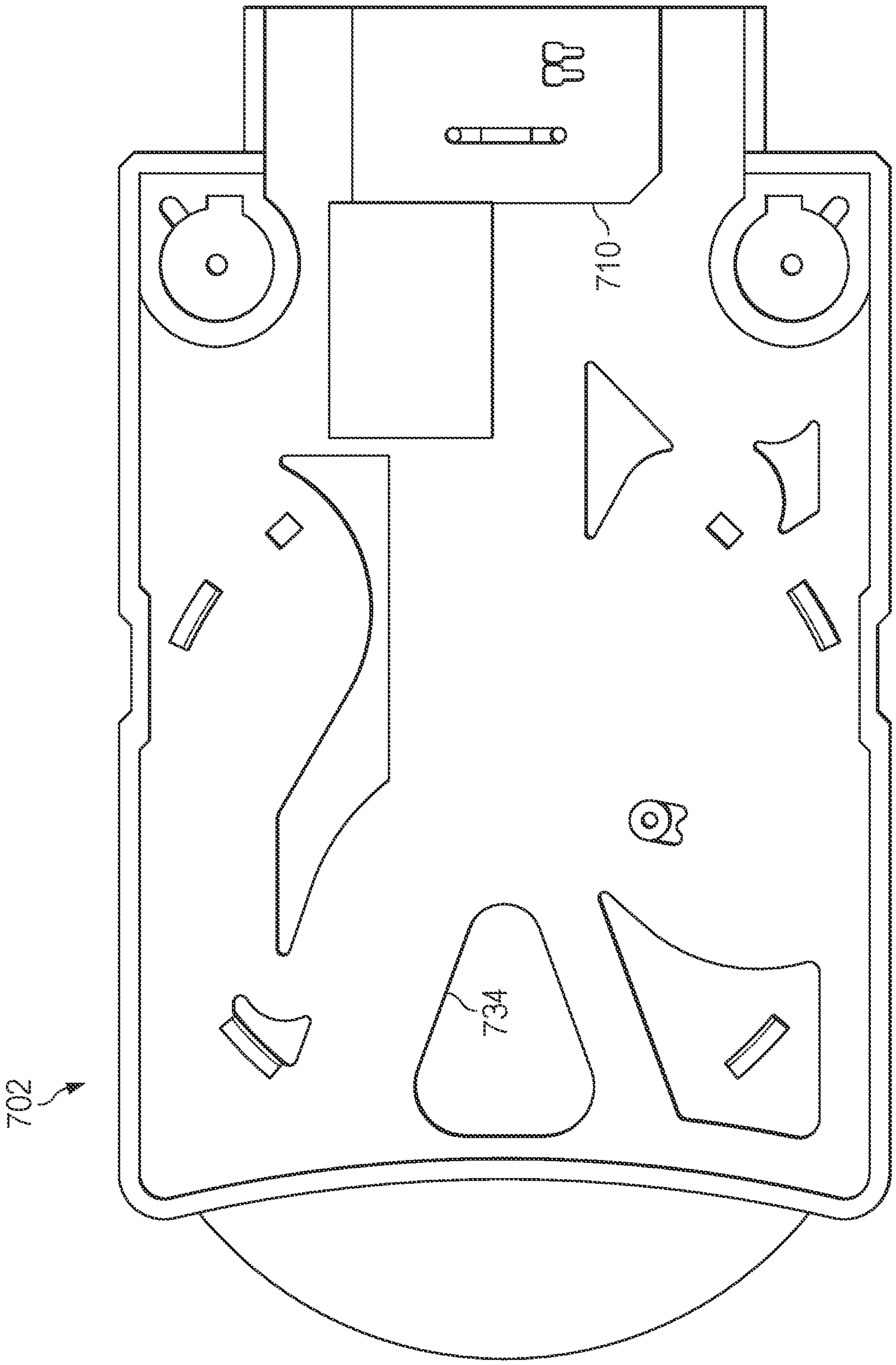
Figure 7E:
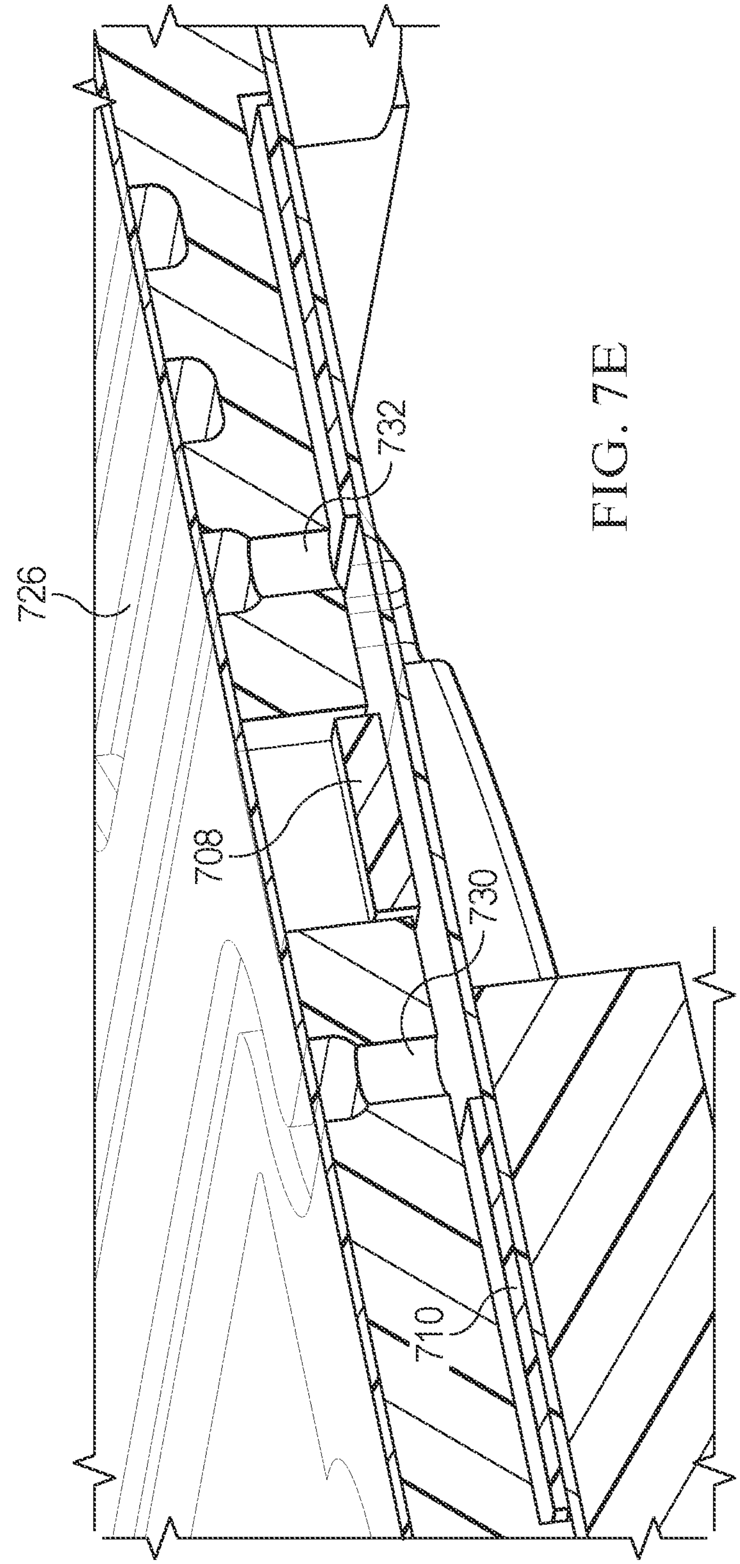
Figure 7F:
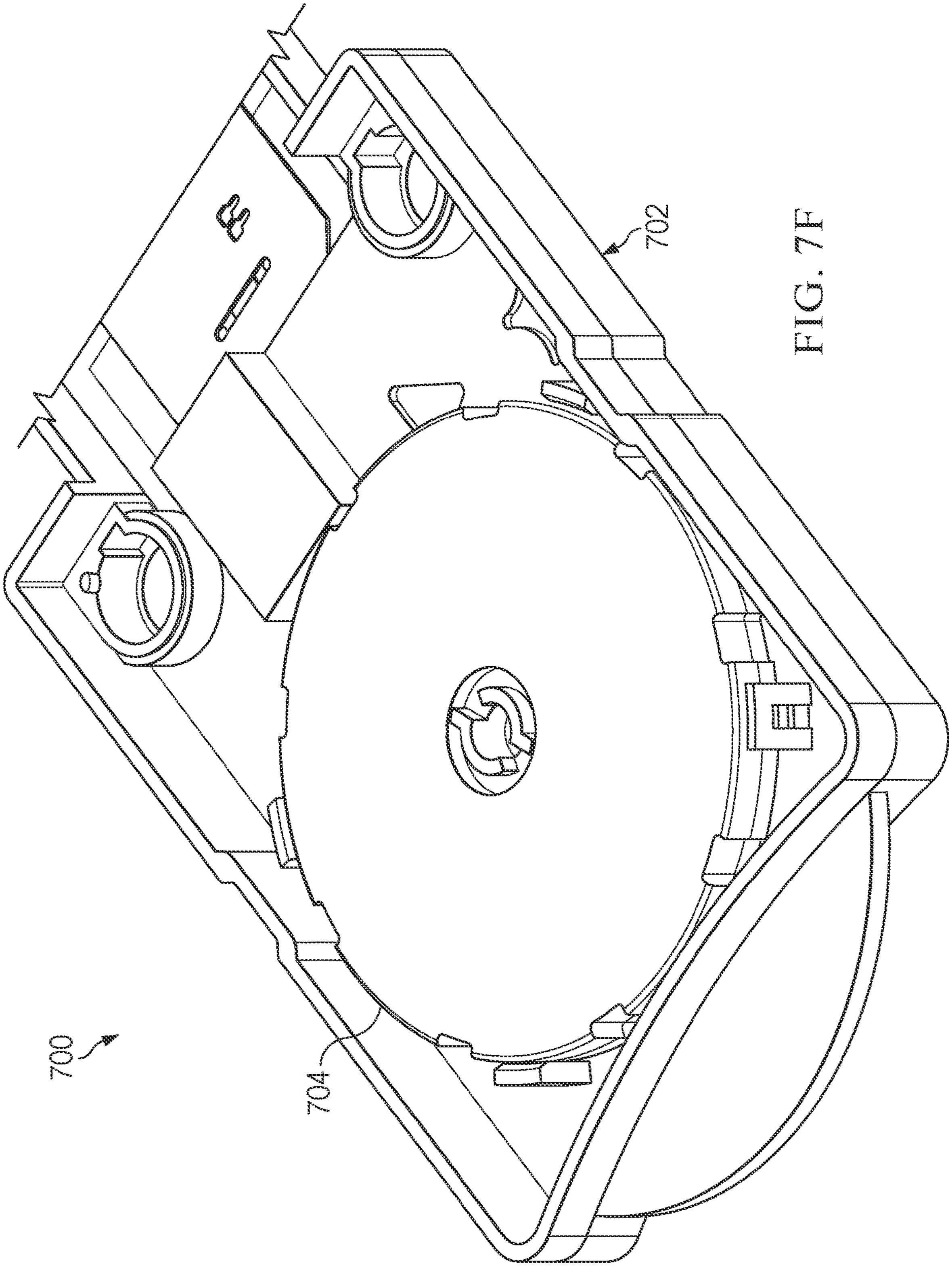
Figure 7G:
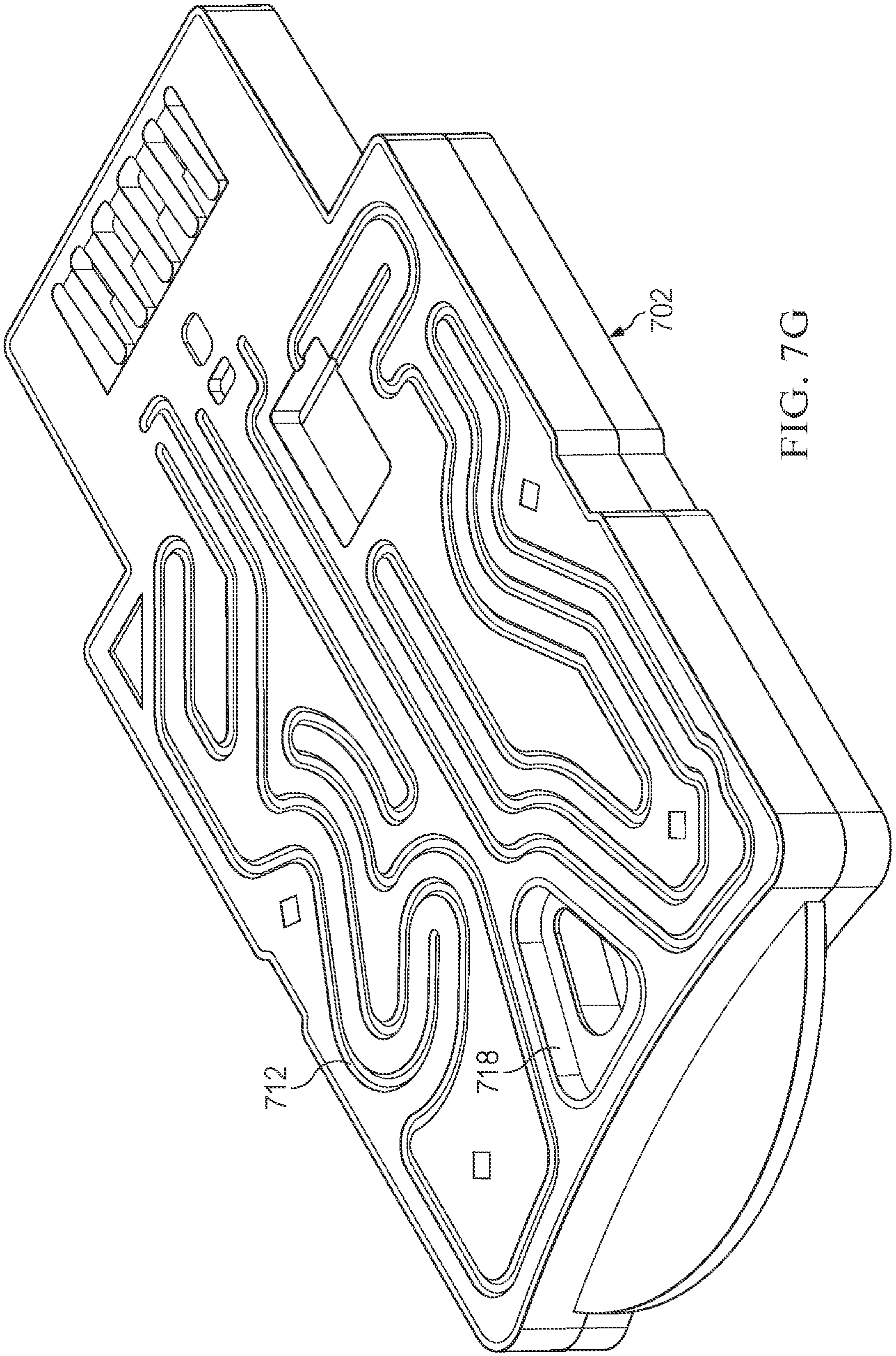

FIG. 7B shows a perspective of a cross section of the sensor assembly when the first portion 702 and the second portion 704 are assembled together to form the sensor assembly. In this figure, the introducer 724 is within the well 718, and has punctured the seal 720. Also visible in this figure is the fluidic pathway 726. FIG. 7C shows a view of the sensor board 710 sitting within the first portion. As seen from this figure, the fluidic pathway includes the sensor 708 via the slot 728 through a first sensor port 730 and a second sensor port 732. FIG. 7D shows a bottom view of the illustrative first portion 702. This view shows the sensor board 710 and a hole 734 to access the sample well. Also seen in this figure are various elements that can assist in seating the second portion correctly with respect to the first portion when the sensor assembly is assembled. FIG. 7E shows a cross section view of the portion of the first portion at the region of the sensor/fluidic pathway region. The illustration in FIG. 7E shows the sensor 708, the sensor board 710, the first sensor port 730, the second sensor port 732, and the overall fluidic pathway 726. FIG. 7F shows a bottom view of the sensor assembly 700 when the first 702 and second 704 portions are assembled together. FIG. 7G shows a top view of the sensor assembly 700 illustrating the first 702 portion and the fluidic pathway 712; and the second portion with only a well 718 visible in this view.

Figure 9A:
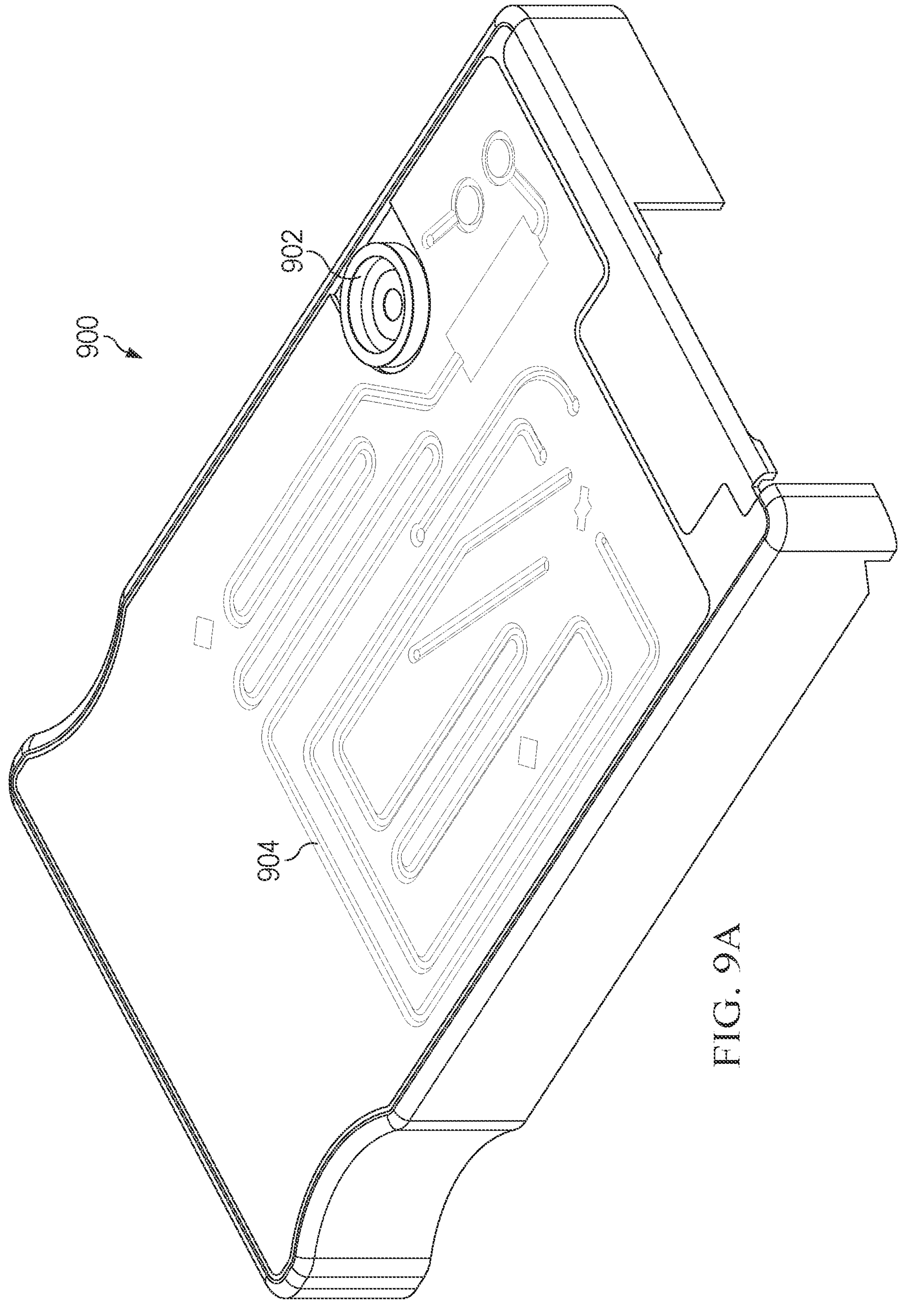
FIGS. 9A to 9C depict various views of an illustrative specific embodiment of a disclosed assembly.
Figure 9B:
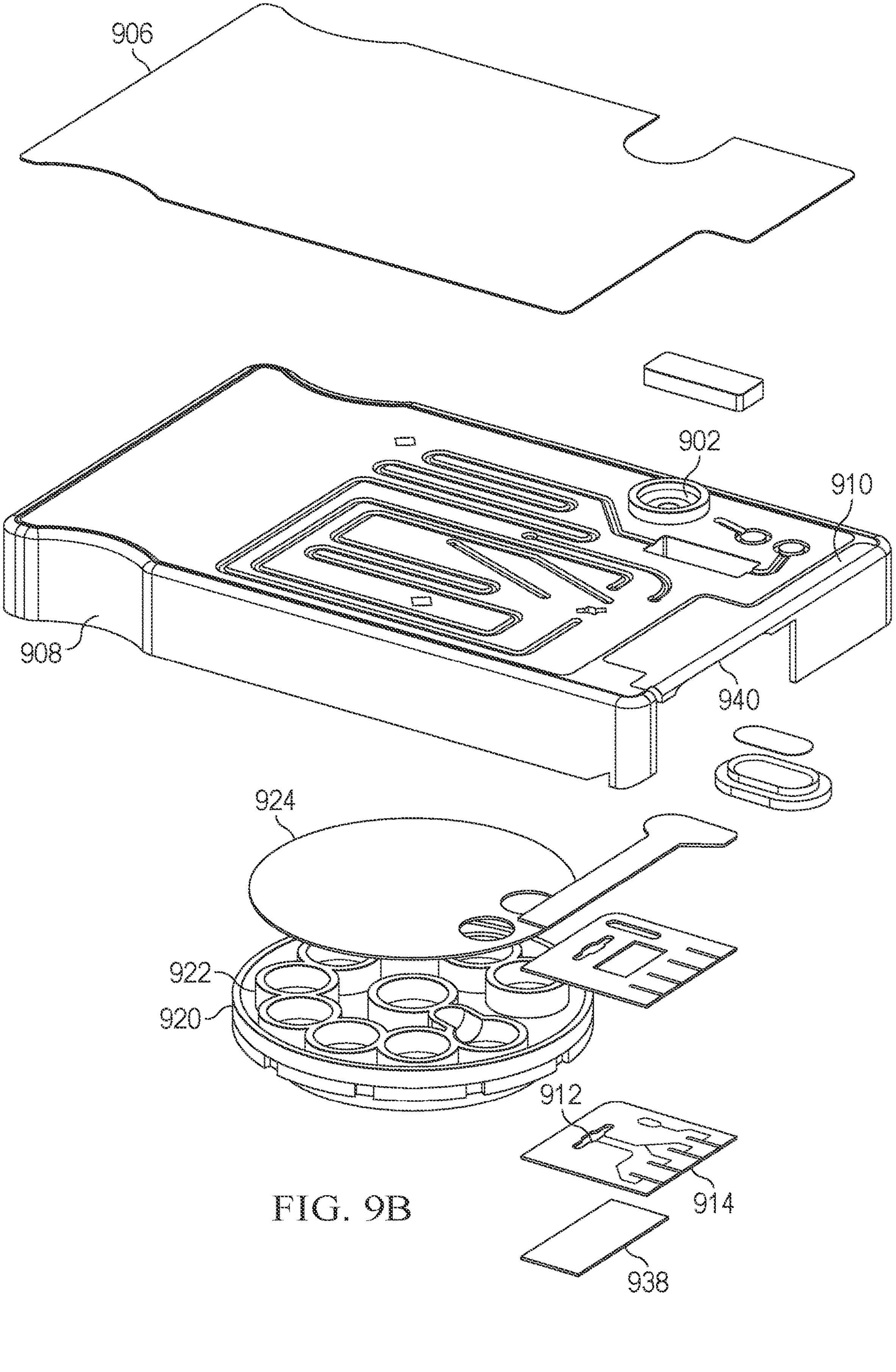
Figure 9C:
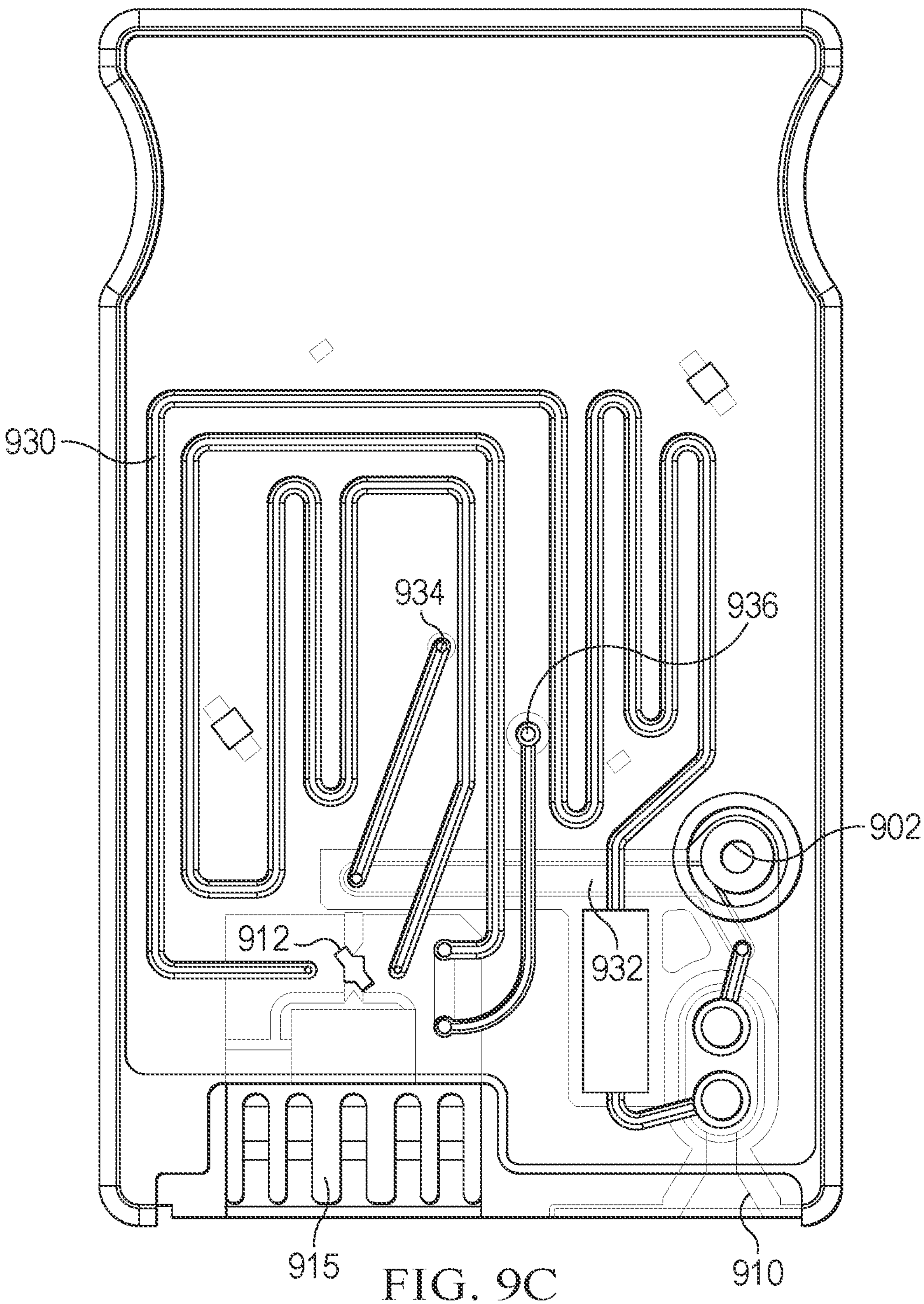

FIGS. 9A to 9C depict an illustrative embodiment of a disclosed assembly. FIG. 9A shows a perspective view of the top of the assembly 900. Visible in this view is a sample introduction chamber 902 and a fluidic pathway 904. As seen from this view, an assembly 900 may be housed in or be configured to have various shapes and sizes. The various shapes and sizes may be chosen, at least in part based on manufacturability, overall usability, size, cost, other factors not discussed herein, or combinations thereof. The sample introduction chamber 902 may be configured so that it can interface with a syringe, a pipette or a disposable dropper for example as is seen in this illustrative embodiment.

FIG. 9B shows a blown-up view of a disclosed assembly in an unassembled fashion. The assembly in FIG. 9B can include a top cover 906. The top cover 906 can be made of any useful material, for example some type of plastic including for example a polyethylene (PET) substrate having a pressure sensitive adhesive thereon. In some embodiments, the top cover 906 may form part of one or more volumes within the fluidic pathway. An illustrative assembly may also include a first portion 908. The illustrative first portion 908 can include at least a fluidic pathway 904 (or part thereof), an introducer (not visible in these figures) and a fluid actuator 910. The illustrative assembly also includes, on or in the first portion 908 a sensor 912 housed on an electrical connection board 914. The electrical connection board 914 may but need not be configured to connect to an external instrument (not shown herein) in a fashion disclosed in commonly assigned and concurrently filed PCT application entitled Interconnect Device and Module Using Same having PCT/US2014/039294 and naming John Tischer as inventor. The electrical connection board 914 is electrically connected to an external instrument (not shown) via an electrical port 940. The electrical port 940 is configured to interface with an opposite but corresponding portion of the external instrument that makes electrical connection with the electrical connections on the electrical connection board 914. This view also shows the sensor 912 that would be within the fluidic pathway once the components are put back together. Also seen in this view is a sensor opposing member 938. The sensor opposing member 938 forms part of the sensor channel along with the sensor 912.

The illustrative assembly disclosed in FIG. 9B may also include a second portion 920. The illustrative second portion may include nine (9) wells with well 922 indicated as an example thereof. The second portion 920 may also include a seal 924. The seal 924 may be configured to cover at least some of the wells in the second portion. In some embodiments, the seal 924 is configured to cover at least those wells that contain one or more materials.

FIG. 9C is a view of the topside of an illustrative first portion of an assembly with various portions removed (for the sake of clarity) and drawn to show features present on both the top and the bottom. Seen therein is the fluid actuator 910. In this illustrative embodiment, the fluid actuator 910 is a port that is configured to connect to fluidly connect with a pump of an external instrument once the assembly is operably disposed within the external instrument. FIG. 9C also shows the region 915 where the electrical connection board having the sensor would be located electrically connected thereto.

Also shown in FIG. 9C is the fluid channel 930 and the sample introduction pathway 932. The sample introduction pathway 932 obtains a sample from the sample introduction chamber 902 transfers it through the sample introduction pathway 932 and deposits it into a well (not shown in FIG. 9C) at sample introduction pathway exit 934. From there, the sample goes into a well and the introducer (not shown in FIG. 9C) transfers the sample into the fluid channel entry 936. The sample is then modulated in the fluid channel 930

(additional material can be added to the sample, the sample and additional material can be mixed, the sample and additional material can be transferred back into a well on the second portion, or any combination thereof) by action of the fluid actuator 910 and eventually flows over the sensor 912 that makes up part of the fluid channel 930. Analytes of interest can then bind to the binding region on or within the sensor 912 modifying something about the sensor. The sensor 912 can communicate with an external instrument (not shown in FIG. 9C) in order to send information about the analyte of interest within the sample.

Thus, embodiments of two-part sensor assemblies are disclosed. The implementations described above and other implementations are within the scope of the following claims. One skilled in the art will appreciate that the present disclosure can be practiced with embodiments other than those disclosed. The disclosed embodiments are presented for purposes of illustration and not limitation.

What is claimed is:

1. A system for detecting a target analyte in a fluid, the system comprising:

a first apparatus, the first apparatus comprising:

a housing and a pathway within the housing for permitting fluid flow inside the housing;

a fluid introducer, configured to be in fluid communication with the pathway for introducing the fluid to the pathway;

a sensor;

an electrical connection board at least partially defining a slot in fluid communication with the pathway; and an offset positioned between the electrical connection board and the sensor, and adjacent to the slot, wherein the offset is electrically connected to and between the sensor and the electrical connection board in a manner to maintain a spacing between the sensor and the electrical connection board;

a second apparatus configured to be connected to the first apparatus, the second apparatus comprising one or more wells;

wherein the second apparatus is configured to be rotated about a point of the housing of the first apparatus to cause the one or more wells to be repositioned from a first position to a second position relative to the fluid introducer; and wherein the fluid introducer is configured to access the fluid from the one or more wells in the first and second positions, and deliver the fluid to the pathway.

2. The system according to claim 1, wherein the one or more wells include at least two wells.

3. The system according to claim 2, wherein at least one well of the at least two wells comprises a seal.

4. The system according to claim 1, wherein the fluid introducer comprises a pipette tip.

5. The system according to claim 1, wherein the sensor is located in the pathway in the first apparatus.

6. The system according to claim 5, wherein the pathway comprises a first sensor port and a second sensor port, and wherein the sensor is disposed in the pathway between the first sensor port and the second sensor port.

7. The system according to claim 5, wherein the first apparatus further comprises a fluid actuator connected to the pathway, and configured to regulate fluid flow in the pathway.

8. The system according to claim 5, wherein the sensor comprises a resonator having a surface configured for binding the target analyte.

9. The system according to claim 5, wherein the sensor is a thin film bulk acoustic resonance (TFBAR) sensor.

10. The system according to claim 5, wherein the first apparatus further comprises a waste wick in fluid communication with the pathway, and the second apparatus further comprises a gasket layer positioned above the one or more wells, wherein the waste wick is configured to contain overflow fluid from the pathway, and the gasket layer is configured to cover at least one well of the one or more wells.

11. The system according to claim 1, wherein the housing of the first apparatus is configured to be moved with respect to the second apparatus.

12. The system according to claim 1, wherein at least a portion of an outer perimeter of the second apparatus is curved.

13. A method comprising:

providing the system according to claim 7;

causing, using the fluid introducer of the first apparatus, the fluid to be obtained from the one or more wells of the second apparatus;

causing, using the fluid introducer, the fluid to be deposited in the pathway of the first apparatus; and actuating, using the fluid actuator of the first apparatus, fluid flow in the pathway to cause at least a portion of the fluid to contact the sensor.

14. The method according to claim 13, further comprising moving the second apparatus with respect to the first apparatus to permit the fluid to be obtained from the at least one well by the fluid introducer.

15. The method according to claim 13, further comprising causing, using the fluid actuator, fluid flow in the pathway in a first direction, and reversing, using the fluid actuator, fluid flow in the pathway to a second direction.

16. The method according to claim 15, further comprising reversing, using the fluid actuator, fluid flow in the pathway at least two times.

17. The device according to claim 1, further comprising an actuator configured to reverse fluid flow in the pathway from a first direction to a second direction.

18. The device according to claim 5, wherein the sensor comprises at least one surface configured for binding the target analyte.

* * * * *